United States Patent
O'Dea et al.

(10) Patent No.: US 9,358,375 B2
(45) Date of Patent: Jun. 7, 2016

(54) FLUID TRANSFER DEVICE AND AN ACTIVE SUBSTANCE CARTRIDGE FOR THE FLUID TRANSFER DEVICE, AND A METHOD FOR CONTROLLING THE PRESSURE AT WHICH AN ACTIVE SUBSTANCE IS DELIVERED TO A SUBJECT FROM A FLUID TRANSFER DEVICE

(75) Inventors: John O'Dea, Bearna (IE); Eoin Bambury, Navan (IE)

(73) Assignee: JANISYS LIMITED, Dangan, Galway (IE)

( * ) Notice: Subject to any disclaimer, the term of this patent is extended or adjusted under 35 U.S.C. 154(b) by 1332 days.

(21) Appl. No.: 13/140,587

(22) PCT Filed: Dec. 21, 2009

(86) PCT No.: PCT/IE2009/000092
§ 371 (c)(1),
(2), (4) Date: Aug. 15, 2011

(87) PCT Pub. No.: WO2010/070628
PCT Pub. Date: Jun. 24, 2010

(65) Prior Publication Data
US 2011/0295230 A1    Dec. 1, 2011

(30) Foreign Application Priority Data

| Dec. 19, 2008 | (IE) | S2008/1010 |
| May 27, 2009 | (IE) | S2009/0410 |
| Aug. 17, 2009 | (IE) | S2009/0629 |
| Aug. 17, 2009 | (IE) | S2009/0630 |

(51) Int. Cl.
*A61M 37/00* (2006.01)
*A61M 5/142* (2006.01)
*A61M 5/28* (2006.01)
*A61M 5/42* (2006.01)

(52) U.S. Cl.
CPC ........... *A61M 37/0015* (2013.01); *A61M 5/282* (2013.01); *A61M 5/425* (2013.01); *A61M2005/14252* (2013.01); *A61M 2037/003* (2013.01); *A61M 2037/0023* (2013.01); *A61M 2037/0061* (2013.01)

(58) Field of Classification Search
CPC ................ A61M 2037/0023; A61M 37/0015; A61M 2005/14252; A61M 5/282; A61M 5/425; A61M 2037/003; A61M 2037/0061
See application file for complete search history.

(56) References Cited

U.S. PATENT DOCUMENTS

| 6,165,155 A * | 12/2000 | Jacobsen et al. ............. 604/156 |
| 2003/0083645 A1 | 5/2003 | Angel et al. |

(Continued)

FOREIGN PATENT DOCUMENTS

| EP | 1992386 A1 | 11/2008 |
| WO | 92/10234 A1 | 6/1992 |

(Continued)

OTHER PUBLICATIONS

International Search Report for PCT/IE2009/000092 dated Apr. 29, 2010.

*Primary Examiner* — Emily Schmidt
*Assistant Examiner* — Lauren M Peng
(74) *Attorney, Agent, or Firm* — Sughrue Mion, PLLC

(57) ABSTRACT

A micro-needle device comprising an active substance layer (3) having a plurality of active substance chambers (4) formed therein, a drive substance layer (9) having a plurality of drive substance chambers (10) formed therein and a needle support layer (5) having a plurality of micro-needles (6) extending therefrom. An activation layer (12) comprising a plurality of heating elements (14) for heating an expandable drive substance (11) located in the drive substance chambers (10) for in turn urging the second membrane (16) into the active substance chamber (4) for pressurizing and urging an active substance (2) therefrom through the corresponding micro-needle (6). A plurality of membrane accommodating recesses (25) extend into the needle support layer (5) for accommodating the first membrane (15) as the active substance in the corresponding active substance chamber (10) is pressurized. A puncturing member (33) with a piercing point (35) extends into each membrane accommodating recess (25). A barrier grating (41) extends across each active substance chamber (4) for preventing contact between the second membrane (16) and the corresponding puncturing member (33).

22 Claims, 11 Drawing Sheets

(56) References Cited

U.S. PATENT DOCUMENTS

2003/0187395 A1   10/2003   Gabel et al.
2006/0264926 A1*  11/2006   Kochamba ........ A61M 5/14248
                                                            606/41
2008/0009805 A1*   1/2008   Ethelfeld ..................... 604/180

FOREIGN PATENT DOCUMENTS

| WO | 02/05889 A1 | 1/2002 |
| WO | 2004/108205 A1 | 12/2004 |
| WO | 2006/016364 A2 | 2/2006 |
| WO | 2008/101892 A1 | 8/2008 |

* cited by examiner

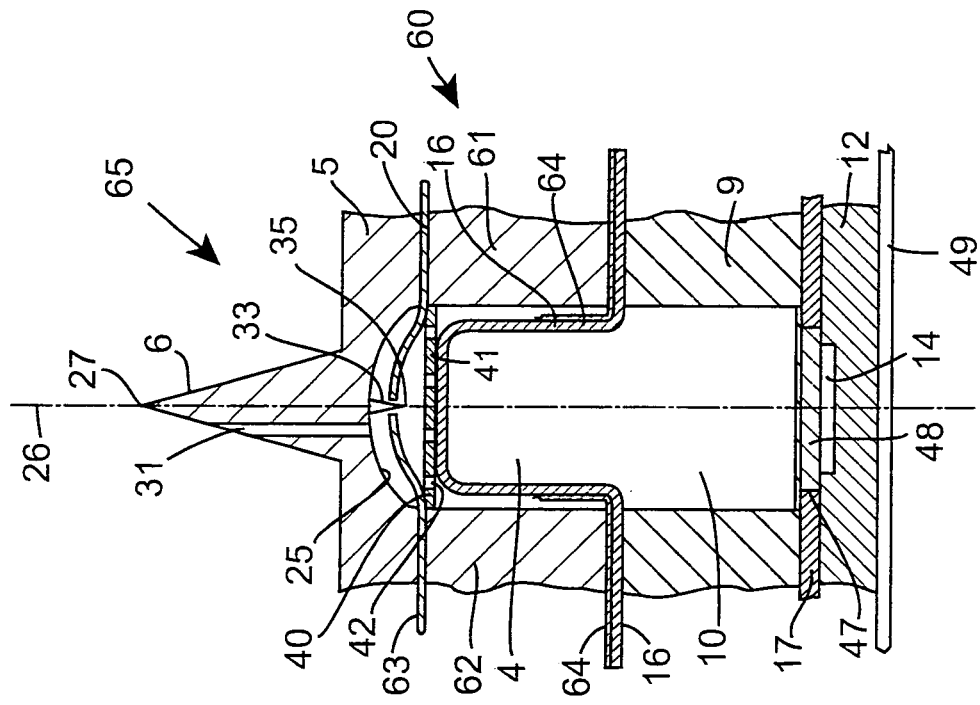
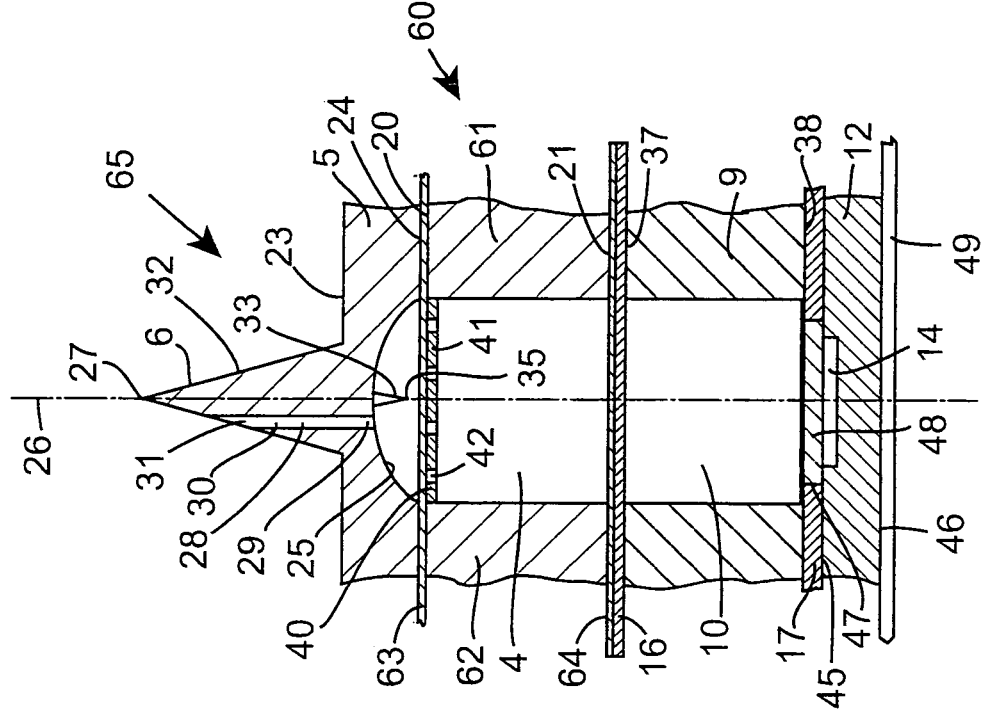

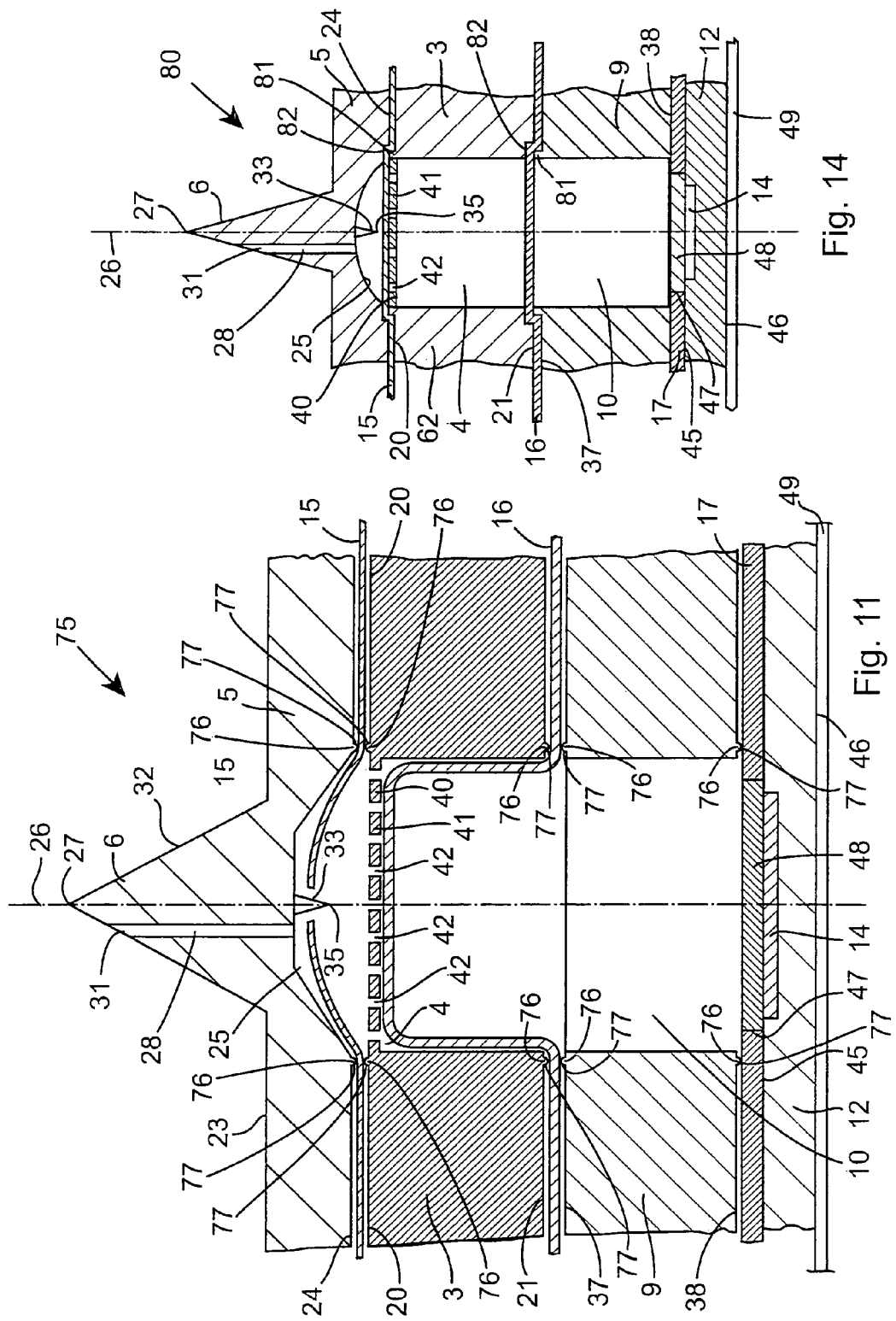

FLUID TRANSFER DEVICE AND AN ACTIVE SUBSTANCE CARTRIDGE FOR THE FLUID TRANSFER DEVICE, AND A METHOD FOR CONTROLLING THE PRESSURE AT WHICH AN ACTIVE SUBSTANCE IS DELIVERED TO A SUBJECT FROM A FLUID TRANSFER DEVICE

BACKGROUND OF THE INVENTION

The present invention relates to a fluid transfer device for transferring a fluid between the device and a subject, and in particular the invention relates to a transfer device for delivering an active substance from the device to a subject intradermally, transdermally, subcutaneously or intramuscularly. The invention also relates to a transfer device for drawing a fluid from a subject. Such devices may be micro-needle devices or otherwise. The invention also relates to an active substance cartridge containing an active substance for use in such a fluid transfer or micro-needle device, and the invention also relates to a method for controlling the pressure at which an active substance is delivered to a subject from a fluid transfer device, such as a micro-needle device.

Micro-needle devices are commonly used for delivering a medicament in fluid form, typically, in liquid form, intradermally, transdermally, subcutaneously and intramuscularly to a subject. Such micro-needle devices, in general, comprise an active substance layer, which typically is of a polymer material defining a first major surface and a second major surface. A plurality of bores, in general, cylindrical bores extend through the active substance layer from the first major surface to the second major surface to form respective active substance chambers for holding similar or different active substances to be delivered to a subject. The bores which form the active substance chambers, in general, are arranged in the form of a matrix.

A needle support layer comprising a plurality of micro-needles extending from a first major surface of the support layer are arranged in a matrix similar to the matrix of the active substance chambers and are aligned with the active substance chambers for accommodating the active substance from corresponding ones of the active substance chambers to the subject. A second major surface of the needle support layer is located adjacent the first major surface of the active substance layer, and a first membrane of a burstable material is located between the second major surface of the needle support layer, and the first major surface of the active substance layer and is sealably secured thereto for sealably closing the active substance chambers adjacent the first major surface of the active substance layer. A plurality of communicating bores extending through the needle support layer extend through corresponding ones of the micro-needles for communicating the active substance chambers with the subject when the first membrane has been burst.

A drive substance layer which defines first and second opposite major surfaces is provided with a plurality of drive substance chambers which are arranged in a matrix similar to the matrix of the active substance chambers, and are aligned with corresponding ones of the active substance chambers. A second membrane of a stretchable material is located between and sealably secured to the second major surface of the active substance layer and the first major surface of the drive substance layer for sealably closing the active substance chambers adjacent the second major surface of the active substance layer and for sealably closing the drive substance chambers adjacent the first major surface of the drive substance layer.

A drive substance, typically, an expandable material which expands under heat is located in the drive substance chambers for urging the stretchable second membrane into the corresponding active substance chambers for pressurising the active substance in the active substance chambers to firstly burst the first membrane adjacent the active substance chambers to communicate the active substance chambers with the corresponding micro-needles for delivering the active substance from the active substance chambers. An activation layer which comprises a plurality of heating elements arranged in a matrix similar to the matrix of the drive substance chambers and aligned with the drive substance chambers is located adjacent the drive substance layer for heating the drive substance contained in the drive substance chambers. A third membrane located between the second major surface of the drive substance layer and a first major surface of the activation layer sealably closes the drive substance chambers.

Such micro-needle devices will be known to those skilled in the art.

However, such micro-needle devices suffer from two relatively serious disadvantages. Firstly, the first membrane of the burstable material which is located between the active substance layer and the needle support layer must be burst adjacent the active substance chamber from which the active substance is to be delivered to the subject in order that the active substance chamber can communicate with the communicating bore of the corresponding micro-needle. The bursting of the first membrane is achieved by pressurising the active substance so that when the pressure of the active substance acting on the first membrane reaches a sufficient bursting pressure, the first membrane adjacent the relevant active substance chamber bursts. However, firstly, there is no guarantee that the pressure of the active substance will be sufficient to burst the first membrane, and secondly, the pressure at which the first membrane is burst may vary relatively dramatically from active substance chamber to active substance chamber depending on the quality and consistency of the first membrane.

A second disadvantage of known micro-needle devices is that it is virtually impossible to control the pressure at which the active substance is delivered to the subject, and thus, it is impossible to control the depth beneath the skin of the subject to which the active substance is delivered to the subject.

These disadvantages are undesirable, and there is therefore a need for a micro-needle device which addresses at least one of the disadvantages of known micro-needle devices.

The present invention is directed towards providing a micro-needle device which addresses at least one of the disadvantages of known micro-needle devices. The invention is also directed towards providing a fluid transfer device for transferring a substance between the device and a subject, and the invention is also directed towards providing an active substance cartridge for use in a micro-needle device or a fluid transfer device. The invention is also directed towards providing a method for controlling the pressure at which an active substance is delivered from a fluid transfer device to a subject.

SUMMARY OF THE INVENTION

According to the invention there is provided a fluid transfer device comprising a first layer having a first face and a first chamber located in the first layer, a skin abutting layer having a first face for abutting skin of a subject and a second face located adjacent the first face of the first layer, a communicating means in the skin abutting layer for accommodating a fluid between the first chamber and the subject, a pressure altering means for altering the pressure in the first chamber for urging the fluid between the first chamber and the subject through the communicating means, a first membrane located between the first face of the first layer and the second face of the skin abutting layer for isolating the communicating means from the first chamber, and a puncturing means located in one of the skin abutting layer and the first layer to be engageable with the first membrane for bursting thereof in response to the pressure altering means altering the pressure in the first chamber.

In one embodiment of the invention the puncturing means extends from one of the skin abutting layer and the first layer and terminates in a piercing means for piercing the first membrane. Preferably, the puncturing means terminates in the piercing means at a location adjacent the first membrane, but slightly spaced apart therefrom.

Advantageously, a membrane accommodating recess extends into the skin abutting layer from the second face thereof, and the puncturing means extends from the skin abutting layer into the membrane accommodating recess towards the first membrane. Preferably, the piercing means of the puncturing means is located within the membrane accommodating recess adjacent a plane defined by the second face of the skin abutting layer, and slightly spaced apart therefrom. Ideally, the piercing means is centrally located in the membrane accommodating recess.

Preferably, the communicating means extends from the membrane accommodating recess. Advantageously, the membrane accommodating recess is communicable with the first chamber.

In one embodiment of the invention the spacing between the piercing means and the first membrane is set to determine the pressure in the first chamber at which the first membrane bursts.

Preferably, the puncturing means comprises an elongated puncturing member terminating in the piercing means.

In one embodiment of the invention the piercing means is defined by a piercing point. Alternatively, the piercing means is defined by a piercing edge.

In another embodiment of the invention the piercing means is defined by an elongated piercing edge. Preferably, the piercing edge defines a sharp cutting edge. Alternatively, the piercing edge defines a serrated edge.

In another embodiment of the invention the piercing edge is inclined relative to the plane defined by the second face of the skin abutting layer for progressively engaging the first membrane. Advantageously, the piercing edge is of partly annular shape. Preferably, the piercing edge extends around a substantial part of the membrane accommodating recess adjacent the periphery thereof.

In one embodiment of the invention the first membrane is moveable from a position spaced apart from the puncturing means into engagement with the puncturing means in response to the pressure altering means altering the pressure in the first chamber. Preferably, the first membrane comprises a burstable material.

In one embodiment of the invention the first membrane comprises a foil material.

In another embodiment of the invention the foil of the first membrane is a metal foil.

Alternatively, the first membrane comprises a polymer film.

In another embodiment of the invention an area of weakness is provided in the first membrane co-operable with the puncturing means for bursting the first membrane.

Preferably, the first membrane is impermeable to the fluid to be transferred between the first chamber and the subject. Advantageously, the first membrane is secured to the first face of the first layer for sealably closing the first chamber adjacent the first face of the first layer.

Preferably, the first membrane is secured to the second face of the skin abutting layer for sealably closing the membrane accommodating recess adjacent the second face of the skin abutting layer.

In one embodiment of the invention a first alignment means is provided for aligning the first chamber in the first layer with the communicating means in the skin abutting layer.

In one embodiment of the invention the first layer comprises a polymer material.

In another embodiment of the invention the skin abutting layer comprises a polymer material.

In a further embodiment of the invention the first layer defines a second face and the first chamber extends into the first layer from the second face, a second membrane being located adjacent the second face of the first layer for closing the first chamber adjacent the second face of the first layer, the pressure altering means being co-operable with the second membrane for urging the second membrane relative to the first chamber for altering the pressure in the first chamber. Preferably, the pressure altering means is co-operable with the second membrane for one of increasing the pressure in the first chamber and decreasing the pressure in the first chamber. Advantageously, the second membrane comprises a stretchable material. Preferably, the second membrane is impermeable to the fluid to be transferred between the first chamber and the subject.

In one embodiment of the invention the second membrane is secured to the second face of the first layer for sealably closing the first chamber adjacent the second face of the first layer.

In another embodiment of the invention the first chamber extends through the first layer from the first face to the second face.

In a further embodiment of the invention a barrier means is provided for preventing engagement of the second membrane with the puncturing means. Preferably, the barrier means is permeable to the fluid to be transferred between the first chamber and the subject. Advantageously, the barrier means is located in the first chamber. Ideally, the barrier means is located adjacent the first face of the first chamber, and advantageously, the barrier means extends across the first chamber.

In one embodiment of the invention the barrier means comprises a perforated barrier panel. Preferably, the barrier panel defines a plurality of openings extending therethrough, the openings being of size to accommodate the fluid to be transferred between the first chamber and the subject, but to prevent the second membrane passing therethrough. Preferably, the barrier means comprises a grating. Advantageously, the barrier means comprises a grill.

In one embodiment of the invention the barrier means defines a portion of the first face of the first layer, and preferably, the first membrane is not secured to the barrier means to facilitate movement of the first membrane relative to the barrier means.

In another embodiment of the invention a second layer is provided having a first face and a second chamber extending into the second layer from the first face thereof, the second layer being located adjacent the first layer with the first face of the second layer adjacent the second face of the first layer, and the second membrane located between the first face of the second layer and the second face of the first layer.

Preferably, the second membrane is secured to the first face of the second layer for sealably closing the second chamber adjacent the first face of the second layer.

In one embodiment of the invention a second alignment means is provided for aligning the first chamber in the first layer with the second chamber in the second layer.

In a further embodiment of the invention the second layer comprises a polymer material.

Preferably, the pressure altering means is located in the second chamber of the second layer.

Advantageously, the second chamber is aligned with the first chamber.

In one embodiment of the invention the pressure altering means comprises a drive substance in the second chamber adapted to one of expand and contract for urging the second membrane to one of increase the pressure in the first chamber and to decrease the pressure in the first chamber.

Preferably, the second membrane is impermeable to the drive substance.

Advantageously, the drive substance comprises an expandable material, and preferably, the drive substance is expandable in response to heat.

In one embodiment of the invention the drive substance comprises a plurality of gas filled polymer micro-beads.

In another embodiment of the invention an activating means is provided for activating the pressure altering means to alter the pressure in the first chamber.

In another embodiment of the invention the second layer defines a second face.

In a further embodiment of the invention an activation layer defining a first face is located adjacent the second layer with the first face of the activation layer adjacent the second face of the second layer, and the activating means is located on the activation layer adjacent the first face thereof for co-operating with the second chamber for activating the pressure altering means therein for one of increasing and decreasing the pressure in the first chamber of the first layer.

Preferably, the pressure altering means is responsive to heat for one of increasing and decreasing the pressure in the first chamber, and the activating means comprises a heating means. Advantageously, the heating means comprises a heating element.

In one embodiment of the invention the heating means comprises an electrically powered heating element.

Preferably, the activating means is aligned with the second chamber.

In one embodiment of the invention the second chamber extends through the second layer from the first face thereof to the second face thereof.

In another embodiment of the invention a third membrane is located between the second face of the second layer and the first face of the activation layer for sealably closing the second chamber adjacent the second face of the second layer. Preferably, the third membrane is of a heat insulating material, and a heat conducting means extends through the third membrane for communicating heat from the heating means to the second chamber. Advantageously, the third membrane is impermeable to the drive substance.

In one embodiment of the invention the third membrane is secured to the second face of the second layer for sealably closing the second chamber adjacent the second face of the second layer.

In another embodiment of the invention a third alignment means is provided for aligning the activating means in the activation layer with the second chamber in the second layer.

Preferably, a penetrating means is provided on the first face of the skin abutting layer for penetrating the skin of the subject. Advantageously, the penetrating means comprises a micro-needle extending from the first face of the skin abutting layer. Ideally, the micro-needle terminates in a distal skin penetrating tip.

In one embodiment of the invention the communicating means extends through the micro-needle.

In another embodiment of the invention the communicating means comprises a first communicating bore extending through the skin abutting layer.

In another embodiment of the invention the communicating means comprises a second communicating bore extending through the micro-needle communicating with the first communicating bore.

In a further embodiment of the invention the micro-needle defines a longitudinally extending central axis, and the second communicating bore extends through the micro-needle offset from the central axis. Preferably, the second communicating bore terminates in an outer surface of the micro-needle spaced apart from the skin penetrating tip.

Alternatively, the communicating means comprises a communicating channel extending along an outer surface of the micro-needle communicating with the first communicating bore extending through the skin abutting layer. Preferably, the communicating channel is recessed into the outer surface of the micro-needle. Advantageously, the communicating channel terminates at a location spaced apart from the distal skin penetrating tip. Preferably, the first communicating bore extends from the membrane accommodating recess.

In one embodiment of the invention the device is adapted for transferring a fluid from the first chamber to the subject, and preferably, the fluid comprises a liquid active substance, and advantageously, the liquid active substance comprises a liquid medicament.

In one embodiment of the invention the first layer comprises a plurality of first chambers, and one communicating means extending through the skin abutting layer is provided corresponding to each first chamber, each communicating means being communicable with the corresponding first chamber.

In another embodiment of the invention a plurality of pressure altering means are provided. Preferably, one pressure altering means is provided corresponding with each first chamber.

Preferably, one puncturing means is provided corresponding to each first chamber.

In another embodiment of the invention a plurality of second chambers are located in the second layer. Preferably, one second chamber is provided corresponding to each first chamber, the second chambers being aligned with the respective first chambers.

In another embodiment of the invention a plurality of micro-needles are provided extending from the first surface of the skin abutting layer. Preferably, one micro-needle is provided corresponding to each first chamber.

In one embodiment of the invention the first chambers are configured in the first layer in a matrix.

In another embodiment of the invention a seal effecting means is provided for effecting a seal between the first membrane and the first layer adjacent the corresponding first chamber.

In one embodiment of the invention each seal effecting means comprises an annular projecting element extending from one of the first face of the first layer and the second face of the skin abutting layer for engaging the first membrane to effect the seal between the first membrane and the first layer. Preferably, each annular projecting element terminates in a radiused membrane abutting surface.

In one embodiment of the invention each annular projecting element extends from the first face of the first layer around the corresponding first chamber. Alternatively, each annular projecting element extends from the second face of the skin abutting layer around the corresponding communicating means.

In another embodiment of the invention a gasket is provided between the first membrane and one of the first layer and the skin abutting layer.

In another embodiment of the invention a gasket accommodating recess extends into the one of the first layer adjacent the first face of the first layer and the skin abutting layer adjacent the second face thereof for accommodating the gasket to co-operate with each annular projecting element extending from the other one of the first layer and the skin abutting layer for effecting the seal between the first membrane and the first layer. Preferably, the gasket is located in the gasket accommodating recess for sealably engaging the first membrane between the gasket and each annular projecting element. Advantageously, the first membrane is located between the gasket and the one or more annular projecting elements. Preferably, the gasket is of a deformable material. Ideally, the gasket is of a resilient deformable material.

Alternatively, a pair of annular projecting elements are provided, one of said annular projecting elements extending from the first face of the first layer and the other of the said pair of annular projecting elements extending from the second face of the skin abutting layer, the respective annular projecting elements co-operating with each other to sealably engage the first membrane therebetween.

In an alternative embodiment of the invention the seal effecting means comprises a pair of interengageable complementary formations, one of the interengageable complementary formations being formed on the first face of the first layer, and the other of the interengageable complementary formations being formed on the second face of the skin abutting layer, the respective formations being located adjacent and extending around the first chamber.

Preferably, one of the interengageable complementary formations comprises an annular projecting element, and the other of the interengageable complementary formations comprises a recess. Advantageously, the annular recess extends into the one of the first face of the first layer around and adjacent the first chamber and the second face of the skin abutting layer around and adjacent the membrane accommodating recess, and the annular projecting element extends from the other one of the first face of the first layer around and adjacent the first chamber and the second face of the skin abutting layer around and adjacent the membrane accommodating recess. Preferably, the annular recess extends into the first face of the first layer.

In another embodiment of the invention a seal effecting means is provided for effecting a seal between the second membrane and the second face of the first layer adjacent the first chamber.

In another embodiment of the invention the seal effecting means comprises an annular projecting element extending from one of the first face of the second layer and the second surface of the first layer for engaging the second membrane to effect the seal between the second membrane and the first layer. Preferably, the annular projecting element terminates in a radiused membrane abutting surface.

In one embodiment of the invention each annular projecting element extends from the first face of the second layer around the corresponding second chamber. Alternatively, each annular projecting element extends from the second face of the first layer around the corresponding first chamber.

In one embodiment of the invention a gasket is provided between the second membrane and one of the first layer and the second layer.

In another embodiment of the invention a gasket accommodating recess extends into the one of the first layer adjacent the second face of the first layer and the second layer adjacent the first face thereof for accommodating the gasket to co-operate with the corresponding annular projecting element extending from the other one of the first layer and the second layer for effecting the seal between the second membrane and the first layer. Preferably, the gasket is located in the gasket accommodating recess for sealably engaging the second membrane between the gasket and each annular projecting element. Advantageously, the second membrane is located between the gasket and the one or more annular projecting elements. Preferably, the gasket is of a deformable material. Advantageously, the gasket is of a resilient deformable material.

In another embodiment of the invention a pair of annular projecting elements are provided, one of said annular elements extending from the second face of the first layer and the other of the said pair of annular projecting elements extending from the first face of the second layer, the respective annular projecting elements co-operating with each other to sealably engage the second membrane therebetween.

In a further embodiment of the invention the seal effecting means comprises a pair of interengageable complementary formations, one of the interengageable complementary formations being formed on the second face of the first layer, and the other of the interengageable complementary formations being formed on the first face of the second layer, the respective formations being located adjacent and extending around the first chamber.

Preferably, one of the interengageable complementary formations comprises an annular projecting ring, and the other of the interengageable complementary formations comprises an annular recess. Advantageously, the annular recess extends into the one of the first face of the second layer around and adjacent the second chamber and the second face of the first layer around and adjacent the first chamber, and the annular projecting element extends from the other one of the first face of the second layer around and adjacent the second chamber, and the second face of the first layer around and adjacent the first chamber.

Preferably, the annular recess extends into the second face of the second layer.

The invention also provides an active substance cartridge comprising a first layer having a first face and a second face and at least one first chamber for an active substance located in the first layer, a first membrane secured to the first face for sealably closing the at least one first chamber adjacent the first face of the first layer, a second membrane secured to the second face of the first layer for sealably closing the at least one first chamber adjacent the second face of the first layer, and a barrier means located in the at least one first chamber for preventing passage of the second membrane across the barrier means, the barrier means being permeable to the active substance.

Preferably, each barrier means extends across the corresponding first chamber. Advantageously, each barrier means is located adjacent the first face of the first layer. Preferably, each barrier means defines a portion of the first face of the first layer.

In one embodiment of the invention the portion of the first face of the first layer defined by each barrier means and the first face of the first layer are coplanar.

Advantageously, the first membrane is not secured to the barrier means so that a portion of the first membrane adjacent each barrier means is moveable relative to the barrier means. Preferably, each barrier means comprises a perforated barrier panel.

In one embodiment of the invention the barrier panel of each barrier means defines a plurality of openings extending therethrough, the openings being of size to accommodate the active substance therethrough, but to prevent the second membrane passing therethrough.

In one embodiment of the invention each barrier means comprises a grating.

In another embodiment of the invention each barrier means comprises a grill.

Preferably, each barrier means is of a polymer material. Advantageously, each barrier means is integrally formed with the first layer.

Preferably, the first layer is of a polymer material.

In another embodiment of the invention the second membrane comprises a foil material.

In another embodiment of the invention the second membrane comprises a metal foil material.

In another embodiment of the invention the second membrane comprises a polymer film.

Alternatively, the second membrane comprises a stretchable material.

Preferably, a plurality of first chambers are provided in the first layer.

In another embodiment of the invention each first chamber comprises an active substance. Preferably, the active substance is a medicament.

In another embodiment of the invention the active substances in the respective first chambers are the same or different.

The invention also provides a fluid transfer device comprising the active substance cartridge according to the invention.

The invention also provides a micro-needle device comprising the active substance cartridge according to the invention.

Further the invention provides the active substance cartridge adapted for use in the fluid transfer device according to the invention with the active substance cartridge according to the invention in place of the first layer and the first membrane of the fluid transfer device.

The invention also provides a micro-needle device comprising a first layer having a first face and a first chamber located in the first layer, a needle support layer having a first face and a second face for locating adjacent the first face of the first layer, a micro-needle extending from the needle support layer adjacent the first face thereof, a communicating means in the needle support layer and the micro-needle for accommodating a fluid between the first chamber and the subject, a pressure altering means for altering the pressure in the first chamber for urging the fluid between the first chamber and the subject through the communicating means, a first membrane located between the first face of the first layer and the second face of the needle support layer for isolating the communicating means from the first chamber, and a puncturing means located in one of the needle support layer and the first layer to be engageable with the first membrane for bursting thereof in response to the pressure altering means altering the pressure in the first chamber.

Further the invention provides a method for controlling the pressure at which an active substance is delivered from a fluid transfer device, the fluid transfer device comprising a first layer having a first face and a first chamber for the active substance located in the first layer, a skin abutting layer having a first face for abutting the skin of the subject and a second face located adjacent the first face of the first layer, skin penetrating means extending from the first face of the skin abutting layer, a communicating means in the skin abutting layer for accommodating the active substance from the first chamber to the subject, a pressure altering means for increasing the pressure in the first chamber for urging the active substance from the first chamber to the subject through the communicating means, a first membrane located between the first face of the first layer and the second face of the skin abutting layer for isolating the communicating means from the first chamber, and a puncturing means located in the skin abutting layer engageable with the first membrane for bursting thereof on movement of the first membrane in response to the pressure altering means increasing the pressure in the first chamber, the method comprising setting the puncturing means relative to the first membrane so that the first membrane engages the puncturing means for bursting thereof when the pressure in the first chamber has increased to a pressure approximately equal to the pressure at which the active substance is to be delivered from the fluid transfer device.

Preferably, the puncturing means is spaced apart from the first membrane, and the spacing between the puncturing means and the first membrane is set.

Advantageously, the puncturing means terminates in a piercing means and the spacing between the piercing means and the first membrane is set.

The advantages of the invention are many. The provision of the puncturing means for puncturing the first membrane ensures that the first membrane is punctured on the active substance being pressurised in the corresponding first chamber. Additionally, by locating the puncturing means in a membrane accommodating recess of the skin abutting layer and by providing the puncturing means with a piercing means which is located within the membrane accommodating recess and by setting the distance between the piercing means and the first membrane at an appropriate distance, the pressure of the active substance in the corresponding first chamber at which the first membrane bursts can be set, and in turn, the pressure at which the active substance is delivered from the first chamber to the subject can likewise be set. This thus permits the injection velocity at which the active substance is delivered to the subject to be set at a desired target injection velocity, so that the depth beneath the skin of the subject to which the active substance is delivered can be set.

By providing the barrier means in the first chamber of the first layer, the second stretchable membrane is separated from the puncturing means, and thus, there is no danger of the second membrane being punctured, and in turn there is no danger of contamination of the active substance with the drive substance.

The provision of the seal effecting means for effecting a seal between the first and second membranes and the corresponding skin abutting layer, first layer and second layer ensures that a good seal is achieved between the respective membranes and the skin abutting layer and the first and second layers, thereby avoiding any danger of leakage of an active substance from one first chamber to an adjacent first chamber and similarly, avoiding any danger of leakage of a drive substance from one second chamber to an adjacent second chamber.

Another advantage of the invention is achieved when the first membrane is stretched taut across the one or more membrane accommodating recesses, in that by stretching the first membrane across the one or more membrane accommodating recesses, the reliability and accuracy with which the pressure of the active substance at which the first membrane engages the piercing means of the puncturing means, and in turn bursts can be set.

BRIEF DESCRIPTION OF THE DRAWINGS

The invention will be more clearly understood from the following description of some preferred embodiments thereof, which are given by way of example only, with reference to the accompanying drawings, in which:

FIG. 7 is a view similar to FIG. 2, and also not to scale, of a portion of a micro-needle device according to another embodiment of the invention, FIG. 8 is a view similar to FIG. 4, and also not to scale, of the micro-needle device of FIG. 7, FIG. 11 is a view similar to FIG. 4 and also not to scale of a micro-needle device according to another embodiment of the invention, FIG. 14 is a view similar to FIG. 2, and also not to scale, of a portion of a micro-needle device according to a further embodiment of the invention.

SUMMARY OF THE INVENTION

Figure 1:
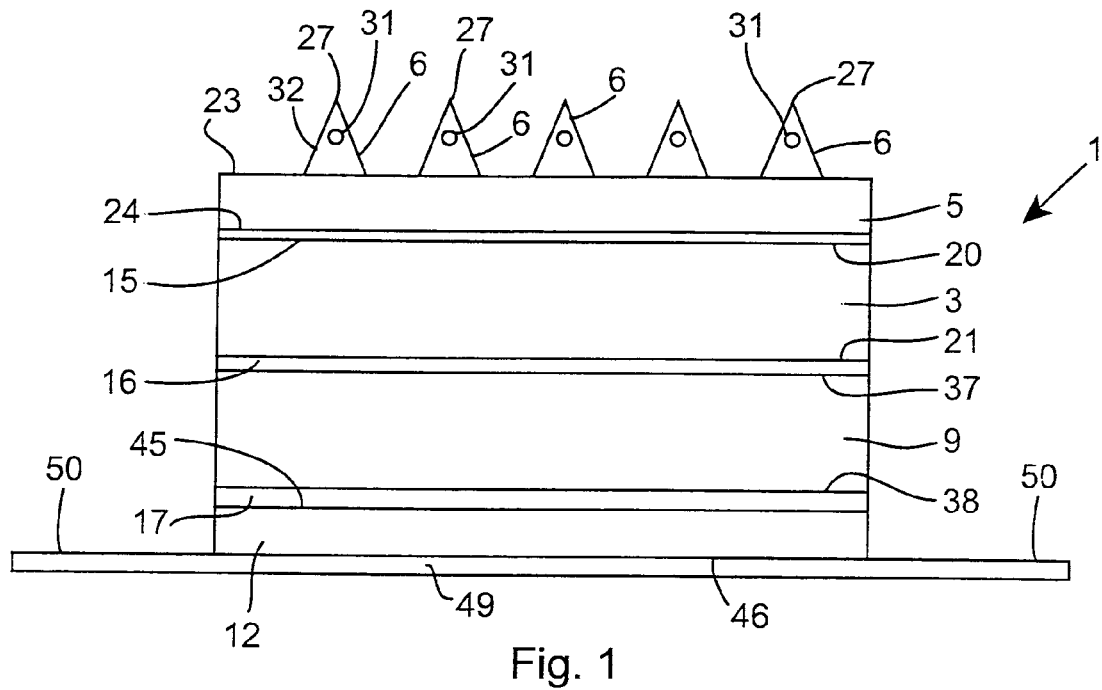
FIG. 1 is a side elevational view not to scale of a micro-needle device according to the invention.
Figure 2:
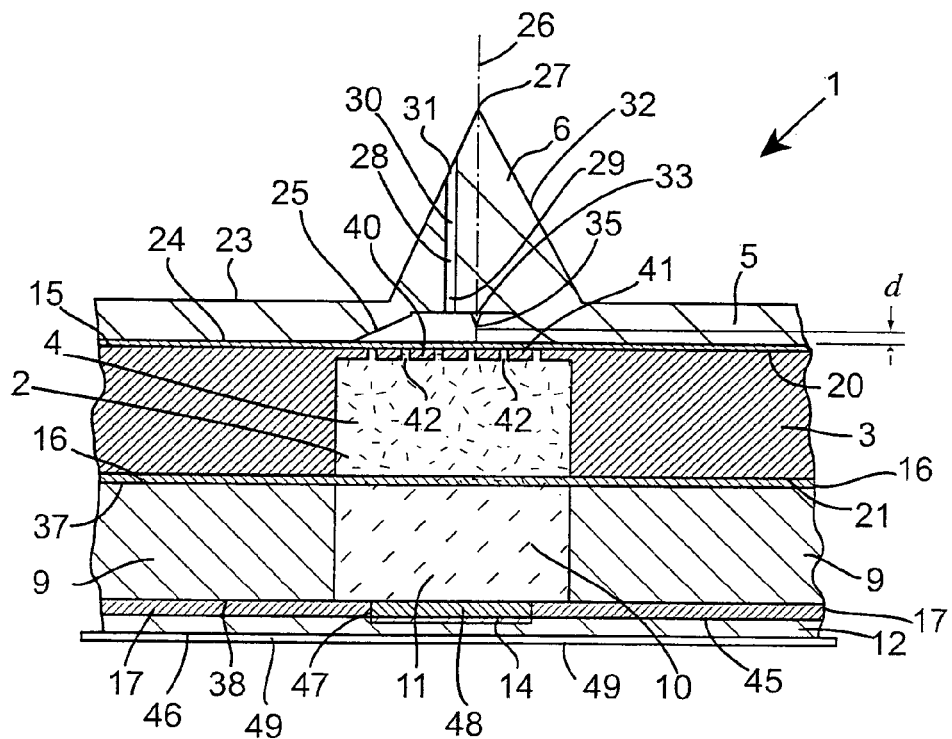
FIG. 2 is a transverse cross-sectional end elevational view, also not to scale, of a portion of the micro-needle device of FIG. 1.
Figure 3:
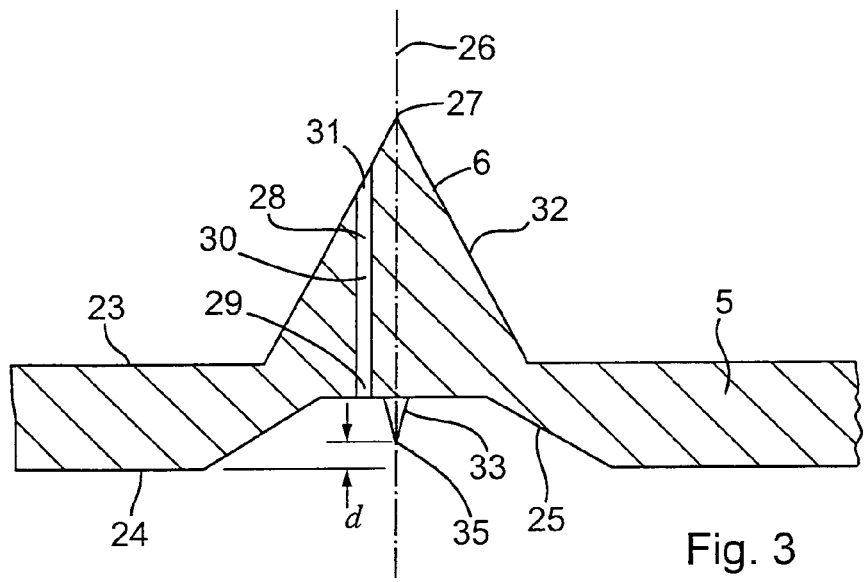
FIG. 3 is an enlarged transverse cross-sectional end elevational view, also not to scale, of a detail of the micro-needle device of FIG. 1.

Referring to the drawings and initially to FIGS. 1 to 5 thereof, there is illustrated a fluid transfer device according to the invention for transferring a fluid between the device and the subject, which in this case comprises a micro-needle device, indicated generally by the reference numeral 1. The micro-needle device 1 is particularly suitable for delivering an active substance in liquid form, for example, a liquid medicament, intradermally, transdermally, subcutaneously as well as intramuscularly to a subject at a preset pressure, so that the active substance 2 is delivered at a target injection velocity to a predetermined depth beneath the skin of the subject. The micro-needle device 1 comprises a first layer, namely, an active substance layer 3 having a plurality of first chambers, namely, active substance chambers 4 for the active substance 2. For convenience in FIGS. 2 and 4 only one active substance chamber 4 is illustrated. A skin abutting layer, namely, a needle support layer 5, is secured to the active substance layer 3 and comprises a plurality of penetrating means for penetrating the skin of a subject, which in this embodiment of the invention are provided by a plurality of micro-needles 6 extending from the needle support layer 5. The micro-needles 6 correspond with and are aligned with the active substance chambers 4 for accommodating the active substance from the corresponding active substance chambers 4 intradermally, transdermally, subcutaneously and/or intramuscularly to the subject.

A second layer, namely, a drive substance layer 9, is secured to the active substance layer 3. The drive substance layer 9 comprises a plurality of second chambers, namely, drive substance chambers 10, in which are located a means for altering the pressure in the active substance chambers 4, which in this embodiment of the invention comprises a drive substance 11. In this case the drive substance 11 increases the pressure in the active substance chambers 4 for urging the active substance 2 therefrom through the micro-needles 6. The drive substance is described in detail below.

An activation layer 12 comprising a plurality of activating means, which in this embodiment of the invention are provided by heating means, namely, electrically powered heating elements 14, is secured to the drive substance layer 9 for activating the drive substance 11 in the drive substance chambers 10 for increasing the pressure in the active substance chambers 4 as will be described in detail below.

A first membrane 15 is located between the active substance layer 3 and the needle support layer 5, a second membrane 16 is located between the active substance layer 3 and the drive substance layer 9, and a third membrane 17 is located between the drive substance layer 9 and the activation layer 12. The first, second and third membranes 15, 16 and 17 are described in detail below.

The active substance layer 3 is of a polymer material and defines a first face, namely, a first major surface 20 and a second face, namely, an opposite second major surface 21. The active substance chambers 4 are formed in the active substance layer 3 by respective cylindrical bores which extend in this case from the second major surface 21 into the active substance layer 3. The active substance chambers 4 are arranged in a matrix in the active substance layer 3, and are adapted for accommodating the active substance 2. It is envisaged that different ones of the active substance chambers 4 may be charged with respective different active substances, depending on a treatment regime under which the subject is to be treated.

The needle support layer 5 defines a first face, namely, a first major surface 23 for abutting the skin of the subject, and from which the micro-needles 6 extend, and a second face, namely, an opposite second major surface 24 which is located adjacent the active substance layer 3. The micro-needles 6 are disposed in a matrix which is similar to the matrix in which the active substance chambers 4 are disposed in the active substance layer 3, and are substantially aligned with the active substance chambers 4, so that one micro-needle 6 is provided corresponding to each active substance chamber 4. A plurality of substantially dome shaped membrane accommodating recesses 25 extend from the second major surface 24 into the needle support layer 5 for accommodating the first membrane 15 therein during pressurising of the corresponding active substance chambers 4 as will be described below. The membrane accommodating recesses 25 are disposed in a matrix which is similar to the matrix in which the micro-needles 6 are disposed and are aligned with the micro-needles 6, and in turn are aligned with corresponding ones of the active substance chambers 4 in the active substance layer 3.

The micro-needles 6 are of conical shape of circular transverse cross-section, and each micro-needle 6 defines a longitudinally extending central axis 26 and terminates in a distal pointed tip 27 for penetrating the skin of the subject. A communicating means, namely, a communicating bore 28 extends through each micro-needle 6 from the corresponding membrane accommodating recess 25 for accommodating the active substance 2 therethrough from the corresponding active substance chamber 4. Each communicating bore 28 defines a first portion 29 which extends through the needle support layer 5 from the corresponding membrane accommodating recess 25, and a second portion 30 which extends from the first portion 29 through the corresponding micro-needle 6. The communicating bore 28 extends through the corresponding micro-needle 6 parallel to the central axis 26 but spaced apart therefrom so that the second portion 30 of each communicating bore 29 terminates in an outlet 31 in an outer surface 32 of the micro-needle 6 at a location spaced apart from the distal tip 27. By offsetting the communicating bore 28 from the central axis 26, so that the communicating bore 28 does not extend through the distal tip 27, coring in the micro-needles 6 is avoided. Coring is caused by a core of tissue being engaged by a communicating bore as the micro-needle is penetrating the skin of the subject. The tissue core in general blocks the communicating bore. In this embodiment of the invention the micro-needles 6 are of sufficient length to penetrate and extend through the stratum corneum.

The first membrane 15 is sealably secured to the first major surface 20 of the active substance layer 3 for sealably closing the active substance chambers 4 adjacent the first major surface 20, and for isolating the active substance chambers 4 from the communicating bores 28 of the corresponding micro-needles 6. Sealably securing the first membrane 15 to the first major surface 20 of the active substance layer 3 prevents leakage of the active substance 2 from one active substance chamber 4 to adjacent active substance chambers 4. The first membrane 15 is also sealably secured to the second major surface 24 of the needle support layer 5 in order to prevent leakage of the active substance from one membrane accommodating recess 25 to adjacent membrane accommodating recesses 25 as the active substance is being delivered to the subject. The first membrane 15, which is impermeable to the active substance 2, is of a burstable material which also has limited stretching properties. Such a burstable material may be provided by a thin film plastics sheet material, for example, a polymer film material, or by a foil, such as a metal foil which may be laminated with a thin plastics film.

A puncturing means comprising a plurality of puncturing members 33 integrally formed with the needle support layer 5 are located in the needle support layer 5 and extend therefrom into the corresponding ones of the membrane accommodating recesses 25. Each puncturing member 33 extends from the needle support layer 5 towards the first membrane 15 and terminates in a piercing means, namely, a piercing point 35 for piercing, and in turn puncturing and bursting the first membrane 15 for communicating the communicating bore 28 of the corresponding micro-needle 6 with the corresponding active substance chamber 4.

Figure 4:
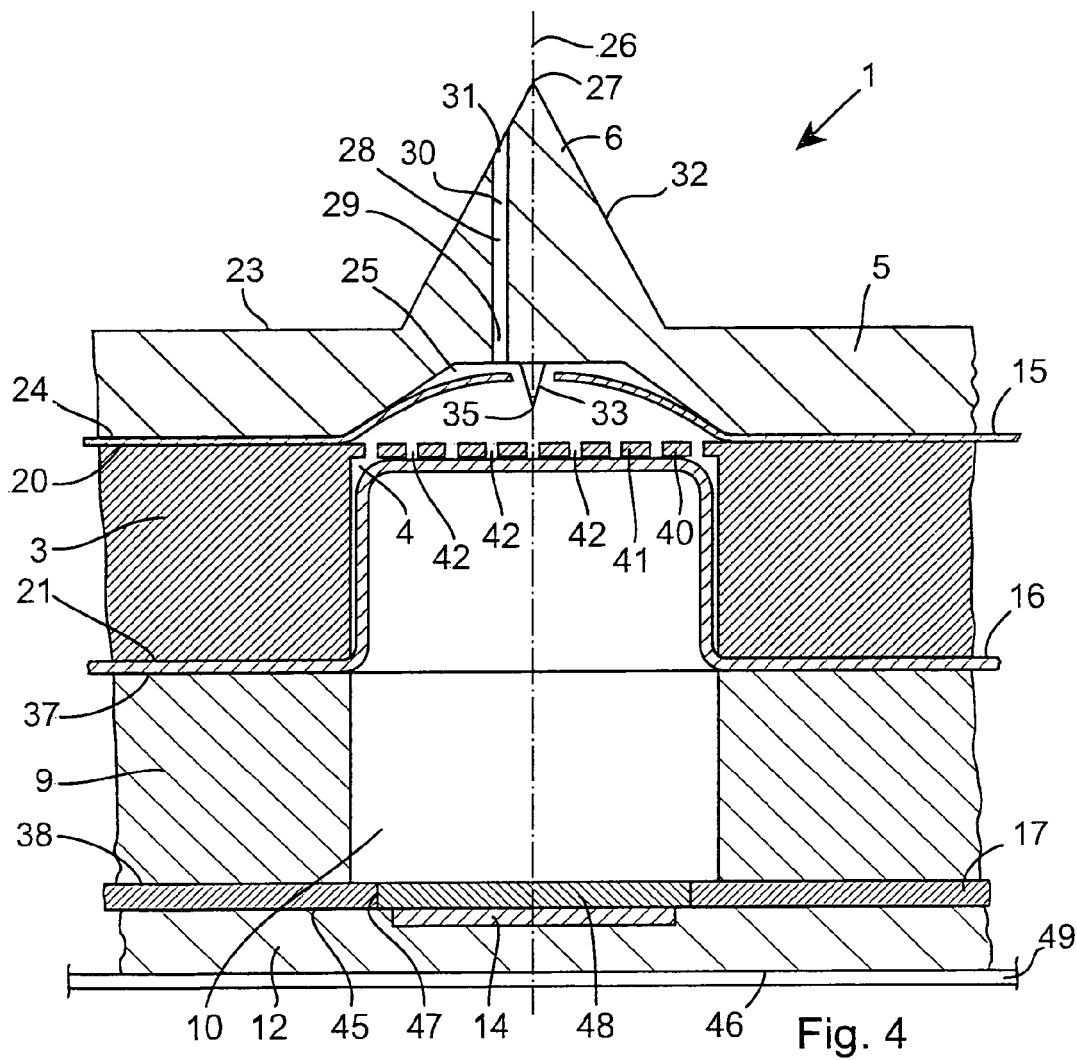
FIG. 4 is an enlarged transverse cross-sectional end elevational view, also not to scale, of the portion of FIG. 2 of the micro-needle device of FIG. 1 in a different state.
Figure 5:
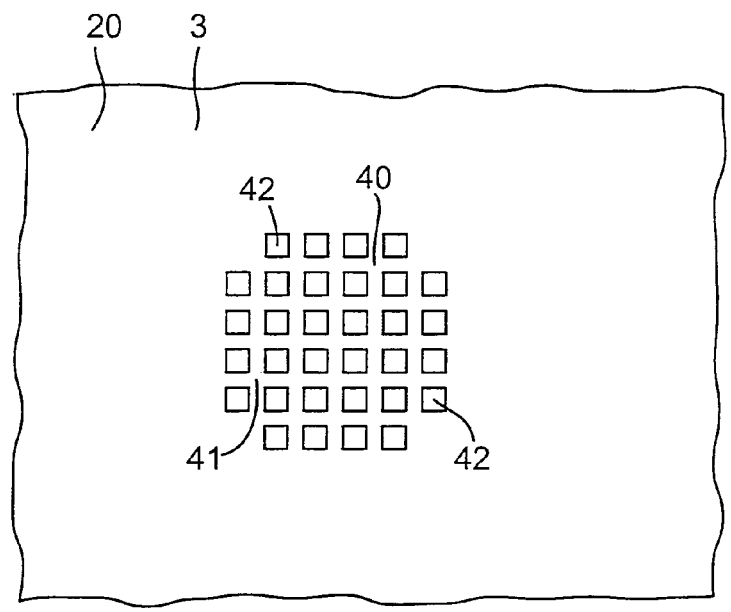
FIG. 5 is a top plan view not to scale of another detail of the micro-needle device of FIG. 1.

Each puncturing member 33 terminates in the corresponding piercing point 35 within the corresponding membrane accommodating recess 25 spaced apart a distance d from a plane defined by the second major surface 24 of the needle support layer 5, and in turn spaced apart the distance d from the first membrane 15. Accordingly, when pressure is applied to the active substance in the corresponding one of the active substance chambers 4, the pressure of the active substance 2 on the first membrane 15 causes the first membrane 15 to expand and balloon into the corresponding membrane accommodating recess 25 as illustrated in FIG. 4. As the pressure of the active substance acting on the first membrane 15 increases, the amount by which the first membrane 15 extends and balloons into the membrane accommodating recess 25 progressively increases, until the first membrane 15 engages the piercing point 35 of the puncturing member 33, thus puncturing, and in turn bursting, and in general, rupturing the first membrane 15 for communicating the communicating bore 28 of the corresponding micro-needle 6 with the corresponding one of the active substance chambers 4.

By setting the distance d by which the piercing point 35 of each puncturing member 33 is spaced apart from the plane defined by the second major surface 24 of the needle support layer 5 and in turn from the first membrane 15, the pressure of the active substance 2 in the corresponding active substance chamber 4 at which bursting of the first membrane 15 takes place can be relatively accurately set. Once the first membrane 15 bursts, the active substance 2 is delivered from the corresponding active substance chamber 4 at the pressure of the active substance at which the first membrane 15 bursts. Therefore, the pressure at which the active substance 2 is delivered from the active substance chambers 4 to the subject can be determined by setting the distance d by which the piercing points 35 of the puncturing members 33 are spaced apart from the second major surface 24 of the needle support layer 5, and in turn from the first membrane 15.

By setting the pressure of the active substance at which the first membrane bursts, the velocity at which the active substance 2 is injected into the subject through the communicating bore 28 of each micro-needle 6 from the corresponding active substance chamber 4 can be determined, and thus set at a target injection velocity value. By setting the injection velocity at which the active substance is delivered into the subject from each micro-needle at a desired target injection velocity value, the depth below the skin of the subject to which the active substance is delivered can likewise be set at a desired depth. By virtue of the fact that the micro-needles 6 extend through the stratum corneum, any resistance which would have been offered to the active substance as it passed through the stratum corneum is avoided, and thereby by setting the injection velocity at a predetermined target injection velocity allows the depth to which the active substance is injected below the skin of the subject to be relatively accurately determined.

In this embodiment of the invention each puncturing member 33 is centrally located on the central axis 26 of the corresponding micro-needle 6 and is also centrally located in the corresponding membrane accommodating recess 25, so that the piercing point 35 engages the first membrane 15 at its point of maximum travel from a plane defined by the second major surface 24 of the needle support layer 5 when the corresponding active substance chamber 4 is pressurised to a predefined pressure. By locating the piercing point 35 of the puncturing member 33 at the position of maximum travel of the first membrane 15 increases the resolution and the reliability at which the pressure of the active substance at which the first membrane bursts can be set.

By being able to set the pressure at which the active substance 2 is delivered to the subject, a major advantage of the micro-needle device 1 according to the invention is achieved, which is discussed above and as is discussed in more detail below.

The drive substance layer 9 is also of a polymer material and defines a first face, namely, a first major surface 37, and a second face, namely, an opposite second major surface 38. The drive substance chambers 10 are formed by cylindrical bores of diameter similar to the diameter of the active substance chambers 4 and extend through the drive substance layer 9 from the first surface 37 to the second surface 38. The drive substance chambers 10 are disposed in a matrix similar to the matrix in which the active substance chambers 4 are disposed, and are aligned with the active substance chambers 4. The drive substance 11 which is provided in the drive substance chambers 10, in this embodiment of the invention is an expandable material which comprises a plurality of gas-filled polymer micro-spheres of the type which are sold under the Trade Mark EXPANCEL, and which are expandable in response to being heated.

The second membrane 16, which is impermeable to the active substance and the drive substance, comprises a stretchable material, which in this embodiment of the invention is a stretchable polymer material, and is sealably secured to the second major surface 21 of the active substance layer 3 for sealably closing the active substance chambers 4 adjacent the second major surface 21. The second membrane 16 is also sealably secured to the first major surface 37 of the drive substance layer 9 in order to sealably close the drive substance chambers 10 adjacent the first major surface 37 thereof. The stretchable material of the second membrane 16 is such as to permit the second membrane 16, on expansion of the drive substance 11 in the drive substance chambers 10, to expand into the corresponding active substance chambers 4 to almost fully define the corresponding active substance chambers 4 in order to pressurise and to substantially fully discharge the active substance from the corresponding active substance chambers 4. The second membrane 16 is illustrated in FIG. 4 in a configuration which substantially fully defines the corresponding active substance chamber 4 for pressurising and discharging the active substance 11 therefrom.

A barrier means, in this embodiment of the invention a perforated barrier panel 40, which is formed by a grating 41 or a grill, is located in each active substance chamber 4 adjacent the first major surface 20 of the active substance layer 3 to prevent the second membrane 16 extending beyond the corresponding active substance chamber 4 into the corresponding membrane accommodating recess 25. By preventing the second membranes 16 extending into the membrane accommodating recesses 25, puncturing of the second membrane 16 by the puncturing member 33 is avoided, and in turn contamination of the active substance with the drive substance is also avoided. Openings 42 in the grating 41 are sized to accommodate the active substance 2 therethrough from the active substance chamber 4 to the communicating bore 28 of the corresponding micro-needle 6. Thus, the barrier panel 40 is permeable to the active substance 2. However, the openings 42 in the grating 41 are of a size so that the barrier panel 40 acts as a barrier to the second membrane 16 passing therethrough into the corresponding membrane accommodating recess 25. In this embodiment of the invention the barrier panels 40 in the respective active substance chambers 4 are of polymer material and are formed integrally with the active substance layer 3 by perforated portions of the active substance layer 3 extending across the active substance chambers 4 adjacent the first major surface 20 of the active substance layer 3.

The activation layer 12 defines a first face, namely, a first major surface 45, and a second face, namely, an opposite second major surface 46. The activation layer 12 is of a substrate material which is suitable for facilitating the formation of a printed circuit thereon, although the activation layer 12 may be of any other suitable material, such as a polymer material, a ceramics material or any other suitable material.

The heating elements 14 are formed on the first major surface 45, and are disposed in a matrix which is similar to the matrix in which the active substance chambers 4 are disposed, and are thus aligned with the corresponding ones of the drive substance chambers 10 for heating the drive substance 11 therein. The heating elements 14 may be formed by electrically resistive elements, such as thick film resistors formed on the substrate forming the activation layer 12 or on a ceramics layer which would also form the activation layer 12. The heating elements 14 are independently addressable, in order to be independently operable so that the drive substance 11 in the drive substance chambers 10 are independently expandable, for in turn independently discharging the active substance 2 from each active substance chamber 4. Electrical circuitry (not shown) is formed on the first major surface 45 of the substrate of the activation layer 12 for facilitating the independent addressing of the heating elements 14. Such an arrangement of heating elements 14 on an activation layer 12 is described in PCT Published Application Specification No. WO 2009/069112 of the present applicant. A programmable microcontroller or microprocessor (neither of which are shown) may be formed in the activation layer 12 or adapted to be secured thereto for controlling the operation of the heating elements 14 as will be described below.

The third membrane 17, which is impermeable to the drive substance, is of a heat insulating material and is sealably secured to the second major surface 38 of the drive substance layer 9 for sealably closing the drive substance chambers 10 adjacent the second major surface 38 of the drive substance layer 9. The third membrane 17 is also sealably secured to the activation layer 12 adjacent the first major surface 45. Openings 47 which correspond with the respective drive substance chambers 10 extend through the third membrane 17 and are sealably closed by heat conductive closure discs 48, typically of a metal material for conducting heat from the heating elements 14 to the corresponding drive substance chamber 10. In this embodiment of the invention the openings 47 are circular, as are the closure discs 48. By providing the third membrane 17 of a heat insulating material, the heat generated by each heating element 14 is directed substantially solely into the drive substance 11 in the corresponding drive substance chamber 10.

Typically, the layers 3, 5, 9 and 12 with the membranes 15, 16 and 17 located therebetween will be tightly clamped together and the layers 3, 5, 9 and 12 will be ultrasonically welded adjacent their respective peripheral edges in order to retain the assembly of the layers 3, 5, 9 and 12 with the membranes 15, 16 and 17 located therebetween tightly and sealably secured together. Alternatively, the assembly of the layers 3, 5, 9 and 12 with the membranes 15, 16 and 17 may be sealably clamped together in a suitable housing. Although not illustrated, alignment means, such as alignment pins may be provided extending from the layers 3, 5, 9 and 12, which would extend through corresponding openings in the corresponding membranes 15, 16 and 17 and which would engage corresponding recesses in the adjacent ones of the layers 3, 5, 9 and 12 may be provided for aligning the layers 3, 5, 9 and 12 with the micro-needles 6, the active substance chambers 4, the drive substance chambers 9 and the heating elements 14 correspondingly aligned with each other.

A means for securing the micro-needle device 1 to the skin of a subject comprises an adhesive patch 49, which is secured to the second major surface 46 of the activation layer 12. A peripheral portion 50 of the patch 49 extends around the periphery of the activation layer 12 for bonding the micro-needle device 1 to the skin of a subject. Alternatively, a strap (not shown) secured to the activation layer 12 may be provided for securing the micro-needle device 1 to the subject. In cases where the layers 3, 5, 9 and 12 with the membranes 15, 16 and 17 therebetween are located in a housing, the adhesive patch 49 or the strap would be secured to the housing. In general, where the micro-needle device 1 is provided for securing to a site of the subject where it is not feasible to secure the micro-needle device 1 with a strap, the micro-needle device 1 is secured with the adhesive patch 49. However, where the micro-needle device 1 is to be secured to a site on the arm or a leg of a subject, the micro-needle device 1 would more typically be provided with a strap which could extend around the arm or leg of the subject and would be secured by a suitable securing means, for example, a buckle, hooks and loops which are sold under the Trade Mark VELCRO or other suitable securing means. On the other hand, where the site is unsuitable for use of a strap to secure the micro-needle device 1 to a site on a subject, the micro-needle device 1 is secured by the patch 49.

In this embodiment of the invention the active substance layer 3 is of thickness of approximately 1.6 mm, and may range in thickness from 0.2 mm to 3.0 mm. The drive substance layer 9 is of thickness of approximately 1.5 mm and may range in thickness from 0.5 mm to 3.0 mm. The active substance chambers 4 and the drive substance chambers 10 are of similar diameter of 2.0 mm, and may range in diameter from 0.5 mm to 10 mm. The needle support layer 5 is of thickness of approximately 0.6 mm and may range in thickness from 0.2 mm to 1.0 mm. The micro-needles 6 are of length of approximately 1.0 mm, and may range in length from 0.3 mm to 3.0 mm. The diameter of each micro-needle 6 adjacent the first major surface 23 of the needle support layer 5 is approximately 0.6 mm, and may range in diameter from 0.2 mm to 1.0 mm. The depth of each membrane accommodating recess 25 is approximately 0.3 from the plane defined by the second major surface 24 of the needle support layer 5 and may range in depth from 0.1 mm to 0.8 mm.

The distance d of the piercing tip 35 of the puncturing member 33 from the plane defined by the second major surface 24 of the needle support layer 5 will be dependent on the pressure of the active substance 2 in the corresponding active substance chamber 4 at which the first membrane 15 is to burst, and will also be dependent on the stretch characteristics of the first membrane 15. However, in general, it is envisaged that the distance d between the piercing point 35 of the puncturing member 33 from the plane defined by the second major surface 24 of the needle support layer 5 will be in the range of 100 microns to 600 microns.

Typically, the first membrane 15 will be of thickness of the order of 5 to 50 microns, the second membrane 16 will be of thickness of the order of 5 to 50 microns and the third membrane 17 will be of thickness of the order of 5 to 50 microns.

In this embodiment of the invention the number of active substance chambers 4 is thirty-six and are arranged in a matrix of six by six. Since the number of drive substance chambers 10 and the number of heating elements 14 and the number of micro-needles 6 is similar to the number of active substance chambers, the micro-needle device 1 comprises 36 micro-needles, 36 drive substance chambers 10, thirty-six heating elements 14 arranged in similar six by six matrices as the six by six matrix of active substance chambers 4.

Returning now to the advantage of setting of the pressure at which the active substance is injected into a subject from the respective active substance chambers 4, as discussed above, by setting the pressure of the active substance 2 at which the first membrane 15 bursts allows the depth beneath the skin of the subject to which the active substance is delivered either intradermally, transdermally, subcutaneously or intramuscularly to the subject to be set. The depth beneath the skin of a subject to which the active substance is delivered is a function of the velocity of the active substance as it exits the outlet 31 of the communicating bore 28 of the corresponding micro-needle 6. The exit velocity of the active substance is a function of the pressure at which the active substance 2 is delivered from the corresponding active substance chamber 4. Thus, the greater the pressure at which the active substance 2 is delivered from the active substance chamber 4, the greater will be the depth beneath the skin of a subject to which the active substance will be delivered.

It is known to use needle-free jet injectors for delivering an active substance transdermally, to a subject, and further it is known that by increasing the pressure at which the active substance is delivered to the subject, the depth beneath the skin of the subject to which the active substance is delivered is increased. However, a problem with this known method using needle-free jet injectors is that the jet of active substance must first penetrate the stratum corneum of the subject. The stratum corneum varies in strength and depth from subject to subject, due to many variables, for example, the age of the subject, the race of the subject, the location in the body of the subject at which the active substance is to be delivered, and the humidity of the environment in which the subject is present during an injection of the active substance. Thus, without knowing the exact strength and depth of the stratum corneum at the precise time at which the active substance is to be delivered by a needle-free jet injector, the depth to which the active substance is delivered intradermally, transdermally, subcutaneously or intramuscularly to a subject cannot be accurately controlled.

However, in the micro-needle device 1 according to the invention, the micro-needles 6 being of sufficient length to extend through the stratum corneum are also of sufficient length so that the outlets 31 from the communicating bores 28 of the micro-needles 6 clear the stratum corneum, and therefore the active substance is accommodated through the micro-needles 6 past the stratum corneum. Accordingly, by accurately setting the pressure at which the first membrane 15 bursts, the pressure at which the active substance 2 is delivered to the subject, and in turn the injection velocity of the active substance is delivered to the subject is accurately set. Thus, the depth to which the active substance 2 is delivered beneath the skin of the subject can likewise be accurately set, since the stratum corneum has been bypassed by the micro-needles 6 of the micro-needle device 1.

Accordingly, to increase the pressure of the active substance in the active substance chambers 4 at which the first membrane 15 bursts requires setting the distance d of the piercing points 35 of the puncturing members 33 at a greater distance from the plane defined by the second major surface 24 of the needle support layer 5. Thus, prior to manufacture of the needle support layer 5, the distance d by which the piercing points 35 of the puncturing members 33 is spaced apart from the plane defined by the second major surface 24 of the needle support layer 5 may be set in order to determine the pressure of the active substance in the corresponding active substance chambers 4 at which the first membrane 15 is to burst. It will be appreciated that the distance d between the piercing points 35 of the puncturing members 33 from the plane defined by the second major surface 24 of the needle support layer 5 may be different from membrane accommodating recess 25 to membrane accommodating recess 25.

By locating each puncturing member 33 and in turn the piercing point 35 thereof centrally in the corresponding membrane accommodating recess 25 on the central axis 26 of the corresponding micro-needle 6, the resolution and in turn the reliability with which the pressure at which the first membrane 15 bursts can be set is maximised. This is due to the fact that the distance of travel of the first membrane 15 from the plane defined by the second major surface 24 of the needle support layer 5 per unit of increase in pressure of the active substance 2 in the corresponding active substance chamber 4 is greatest along the central axis 26 of the corresponding micro-needle 6, which coincides with the centre of the membrane accommodating recess 25.

In use, the needle support layer 5 is produced with the piercing points 35 of the puncturing members 33 at the appropriate distance d from the plane defined by the second major surface 24 of the needle support layer 5. Where the micro-needle device 1 is required to deliver one or more active substances to the same depth beneath the skin of the subject, the distance d of the piercing points 35 of the puncturing members 33 from the plane defined by the second major surface 24 of the needle support layer 5 will be similar. However, where the active substance or active substances are to be delivered to different depths beneath the skin of the subject, the distance d of the piercing points 35 of the puncturing members 33 from the plane defined by the second major surface 24 of the needle support layer 5 will be different from puncturing member 33 to puncturing member 33 and will be set depending on the depth beneath the skin of the subject to which the active substance or substances in the corresponding active substance chamber 4 or chambers 4 are to be delivered to the subject.

Typically, in assembling the micro-needle device 1, the second membrane 16 is sealably secured to the second major surface 21 of the active substance layer 3 to sealably close the active substance chambers 4 adjacent the second major surface 21. The active substance chambers 4 are then charged with the active substance or active substances, depending on whether the micro-needle device 1 is to be provided to deliver one type of active substance or different types of active substances to a subject. The first membrane 15 is then sealably secured to the first major surface 20 of the active substance layer 3 in order to sealably retain the active substance or the active substances in the active substance chambers 4.

The third membrane 17 with the closure discs 48 sealably located in the openings 47 is then sealably secured to the second major surface 38 of the drive substance layer 9, and the drive substance chambers 10 are charged with the drive substance 11. The drive substance layer 9 is then secured to the active substance layer 3 by sealably securing the first major surface 37 of the drive substance layer 9 to the second membrane 16. The activation layer 12 with the adhesive patch 49 secured to the second major surface 46 is secured to the assembled active substance layer 3 and the drive substance layer 9 by securing the activation layer 12 to the third membrane 17.

The needle support layer 5 is then secured to the assembled active substance layer 3, the drive substance layer 9 and the activation layer 12 by sealably securing the second major surface 24 of the needle support layer 5 to the first membrane 15.

During assembly of the needle support layer 5, the active substance layer 3, the drive substance layer 9 and the activation layer 12, the active substance chambers 4 are aligned with the corresponding drive substance chambers 9, which in turn are aligned with the heating elements 14, and the micro-needles 6 are aligned with the active substance chambers 4, so that corresponding ones of the micro-needles 6, the active substance chambers 4, the drive substance chambers 9 and the heating elements 14 are appropriately aligned with each other.

Typically the first, second and third membranes 15, 16 and 17 are sealably secured to the corresponding ones of the needle support layer 5, the active substance layer 3, and the drive substance layer 9 by ultrasonic welding, although the membranes 15, 16 and 17 may be sealably secured to the layers 3, 5 and 9 by a suitable adhesive. However, it should be noted that the first membrane 15 is not secured or bonded to the barrier panels 40 in the active substance layer 3, in order to facilitate ballooning of the first membrane 15 into the respective membrane accommodating recesses 25.

Prior to securing the micro-needle device 1 to the subject, the microprocessor (not shown), which as discussed above, may be incorporated in the activation layer 12 or secured thereto, is programmed to dispense the active substance or the active substances to the subject in accordance with a suitable treatment regime. For example, the microprocessor could be programmed to provide a treatment regime over a five- or a seven-day period. Where the micro-needle device is adapted to administer only one active substance to a subject, programming of the microprocessor (not shown) requires selecting the appropriate number of heating elements to be activated in order to produce a dose of the active substance of the appropriate volume. In other words, the microprocessor is programmed so that the appropriate number of heating elements are activated to pressurise the active substance 2 in an appropriate number of the active substance chambers 4 to produce a dose of the active substance of the required volume. Programming of the microprocessor also requires inputting the number of doses to be administered to the subject per day, and the times during the day or night at which the doses are to be administered to the subject. Once programmed, the micro-needle device is ready to be attached to the subject.

Where the micro-needle device 1 is adapted to deliver more than one active substance to a subject, programming requires inputting of the number of heating elements to be activated to produce doses of the respective active substances, and also the times of the day or night at which the doses of the respective active substances are to be administered to the subject.

The micro-needle device 1 may also be used to provide a treatment regime over a much shorter time duration, for example, a half hour period, a one hour period, a half day period, a one or a two day period as desired.

With the micro-needle device 1 appropriately programmed and secured to an appropriate site on the subject with the micro-needles 6 penetrating through the stratum corneum of the subject, and with the outlets 31 of the communicating bores 28 clear of the stratum corneum, on activation of one or more of the heating elements 14, the drive substance 11 in the corresponding drive substance chambers 10 expands, thereby urging the second membrane 16 into corresponding ones of the active substance chambers 4 to pressurise the active substance 2 therein. The rising pressure of the active substance 2 in the active substance chambers 4 urges the first membrane 15 to balloon into the corresponding membrane accommodating recesses 25. On the pressure of the active substance in the active substance chambers 4 being at the set pressure at which the active substance is to be delivered to the subject, the ballooning first membrane 15 engages the piercing points 35 of the puncturing members 33 in the corresponding membrane accommodating recesses 25. The first membrane 15 is then punctured and bursts, thereby communicating the active substance chambers 4 with the communicating bores 28 of the corresponding micro-needles 6, which correspond with the heating elements 14 which have been activated. On bursting of the first membrane 15, the second membrane 16 is urged further into the corresponding active substance chamber 4, thus maintaining the pressure on the active substance in the active substance chamber 4 at the desired set pressure, and the active substance is delivered from the active substance chamber 4 at the set pressure, and in turn at the target injection velocity, by the action of the second membrane 16 continuing to expand into the active substance chamber 4 under the action of the drive substance in the corresponding drive substance chamber 10.

During the treatment period during which the subject is to be subjected to the treatment regime, the appropriate ones of the heating elements 14 are activated at the appropriate times in order to administer respective doses of the active substance or active substances of the appropriate volume at the appropriate times over the five- to seven-day period of the treatment regime. However, in certain cases, it is envisaged that each active substance chamber 4 may comprise an appropriate amount of the active substance to constitute one dose of the active substance, and in which case, only one heating element 14 will be activated in order to administer a dose of the active substance to the subject.

Figure 6:
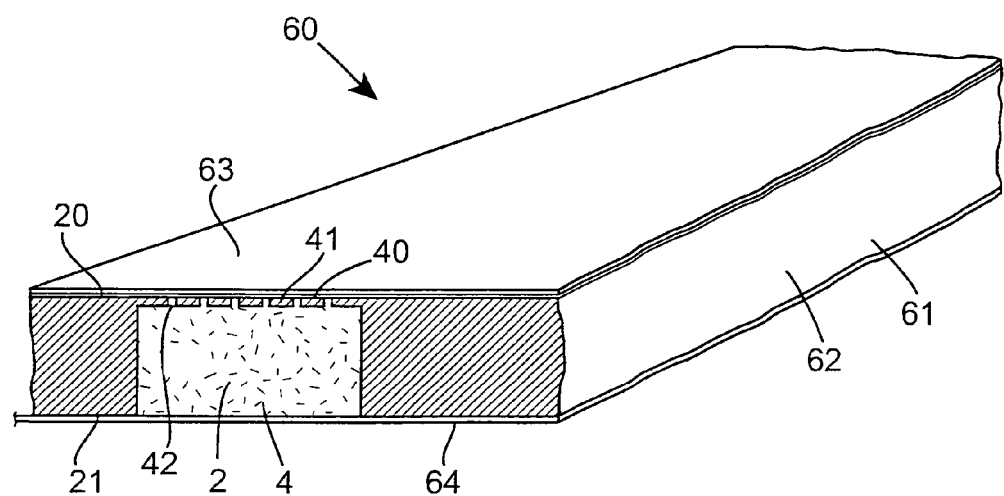
FIG. 6 is a perspective view not to scale of an active substance cartridge also according to the invention for a micro-needle device.

Referring now to FIG. 6, there is illustrated a portion of an active substance cartridge according to the invention, indicated generally by the reference numeral 60, for use with a micro-needle device substantially similar to the micro-needle device 1 described with reference to FIGS. 1 to 5. In this embodiment of the invention the active substance cartridge 60 comprises an active substance cartridge element 61 which is formed by an active substance layer 62 which is similar to the active substance layer 3 of the micro-needle device 1, and similar components are identified by the same reference numerals. The active substance layer 62 comprises a plurality of active substance chambers 4 disposed in a matrix, and extending from a second major surface 21 of the active substance layer 62 and terminating adjacent a first major surface 20 of the active substance layer 62 in a barrier panel 40 provided by a grating 41. For ease of illustration only one active substance chamber 4 is illustrated. A first membrane 63 which is similar to the first membrane 15 of the micro-needle device 1 is sealably secured to the first major surface 20 of the active substance layer 62 for sealably closing the active substance chambers 4 adjacent the first major surface 20, but is not secured to the barrier panel 40. A second membrane 64 of a stretchable material, which is similar to the second membrane 16 of the micro-needle device 1 is sealably secured to the second major surface 21 of the active substance layer 62 for sealably closing the active substance chambers 4 adjacent the second major surface 21.

The grating 41 is similar to the grating 41 of the micro-needle device 1, and is formed in each active substance chamber 4 adjacent the first major surface 20 of the active substance layer 62 for accommodating the active substance therethrough, and for preventing travel of the second membrane 64 past the grating 41.

Otherwise, the active substance cartridge 60 is similar to the active substance layer 3 when the first membrane 15 and the second membrane 16 are sealably secured to the active substance layer 3 of the micro-needle device 1.

In use, the active substance cartridge 60 will be precharged with the active substance. In general, after one of the first membrane 63 and the second membrane 64 has been sealably secured to the active substance layer 62, the active substance chambers 4 will be charged with the one or more active substances, and then the other of the first and second membranes 63 and 64 will be sealably secured to the active substance layer 62. It is envisaged that the active substance cartridge 60 would be sold separately to be subsequently secured to a needle support layer 5 and a drive substance layer 9 by, for example, a doctor, a paramedic or the like.

Additionally, it is envisaged that the drive substance layer could be provided as drive substance cartridge with the drive substance chambers thereof already charged with the drive substance. The drive substance cartridge would be provided with a third membrane similar to the third membrane 17 sealably secured to the second major surface 38 of the drive substance layer, and a second membrane, similar to the second membrane 16 would be sealably secured to the first major surface 37 of the drive substance layer 9. Thus, in this case the micro-needle device when assembled with the active substance cartridge 60 according to the invention and a drive substance cartridge pre-charged with the driving substance, two second membranes would be provided between the active substance layer 62 and the drive substance layer, which would be secured together, one second membrane being sealably secured to the first major surface 37 of the drive substance layer 9, and the other second membrane being secured to the second major surface 21 of the active substance layer 62. Both second membranes would be sufficiently stretchable to stretch into the corresponding active substance chambers 4 to substantially define the active substance chambers 4 as illustrated and described with reference to FIG. 4.

Alternatively, it is envisaged that the second membrane which would be secured to the second major surface 21 of the active substance layer 62 may be provided as a burstable membrane, which on being subjected to pressure from the second stretchable membrane which would be attached to the first major surface 37 of the drive substance layer 9 would burst, thus allowing the second stretchable membrane 16 which would be attached to the first major surface 37 of the drive substance layer 9 to expand into the corresponding active substance chamber 4 in the active substance layer 62 to substantially define the active substance chambers 4.

Referring now to FIGS. 7 and 8, there is illustrated a portion of a micro-needle device also according to the invention and indicated generally be reference numeral 65. The micro-needle device 65 is assembled from the active substance cartridge 60 described with reference to FIG. 6. The micro-needle device 65 is substantially similar to the micro-needle device 1 and similar components are identified by the same reference numerals. In this embodiment of the invention the active substance cartridge is provided with a first membrane 62 of a burstable polymer film material, and a second membrane 64 also of a burstable polymer film material. The second stretchable membrane 16 which is secured to the first major surface 37 of the drive substance layer 9 is of a similar stretchable material to that of the second membrane 16 of the first micro-needle device 1. Thus, as illustrated in FIG. 8, on activation of the heating elements 14 of the activation layer 12, the drive substance in the corresponding drive substance chambers 10 expands, thus urging the second stretchable membrane 16 which is secured to the drive substance layer 9 against the second burstable membrane 64, which is secured to the second major surface 21 of the active substance layer 62. The action of the second stretchable membrane 16 on the second burstable membrane 64 bursts the second membrane 64. This in turn allows the second stretchable membrane 16 to be urged into the corresponding active substance chambers 4 by the drive substance in the corresponding drive substance chambers 10, so that the second stretchable membrane 16 substantially defines the corresponding active substance chambers 4 for urging the active substance therefrom.

Figure 10:
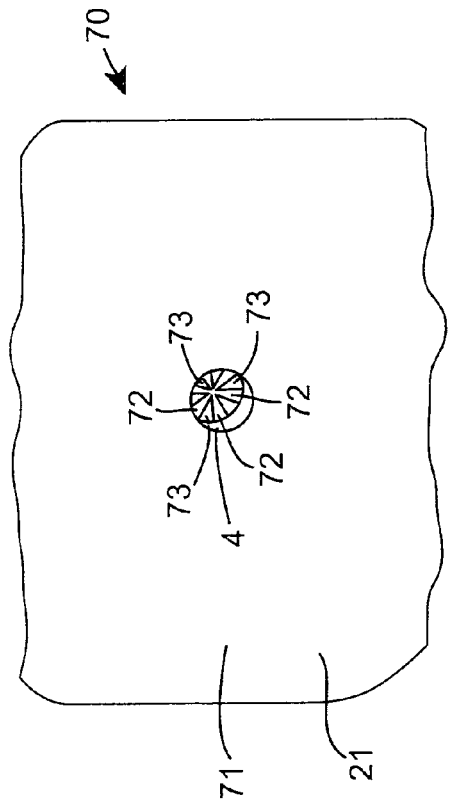
FIG. 10 is an underneath perspective view not to scale of the portion of FIG. 9 of the micro-needle device according to the embodiment of the invention of FIG. 9.
Figure 9:
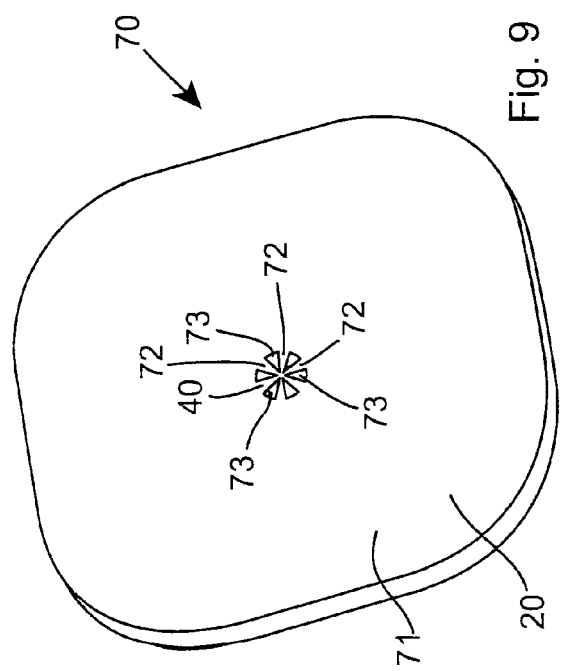
FIG. 9 is a top perspective view not to scale of a portion of a micro-needle device according to another embodiment of the invention.

Referring now to FIGS. 9 and 10, there is illustrated a portion 70 of an active substance layer 71 of a micro-needle device according to another embodiment of the invention. The active substance layer 71 in this embodiment of the invention is similar to the active substance layer 3 of the micro-needle device 1, as is the micro-needle device substantially similar to the micro-needle device 1, and similar components are identified by the same reference numerals. The main difference between the active substance layer 71 of this embodiment of the invention and that of the micro-needle device 1 described with reference to FIGS. 1 to 5 is in the perforated barrier panel 40. In this embodiment of the invention the barrier panel 40 is provided by a plurality of members 72 radiating outwardly from a central axis defined by the corresponding active substance chamber 4 so that the radial members 72 define active substance accommodating openings 73 for accommodating the active substance from the active substance chamber 4 to the communicating bore of the corresponding micro-needle.

Figure 12:
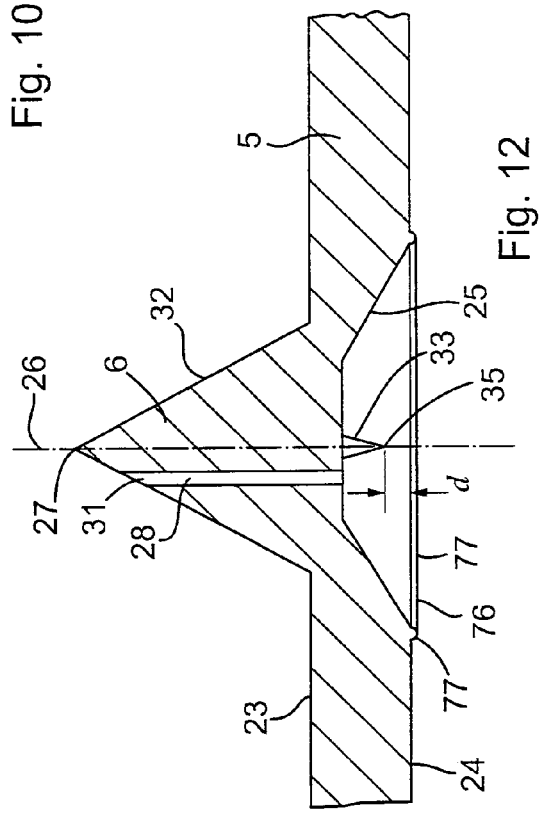
FIG. 12 is a view similar to FIG. 3 and also not to scale of a detail of the micro-needle device of FIG. 11.
Figure 13:
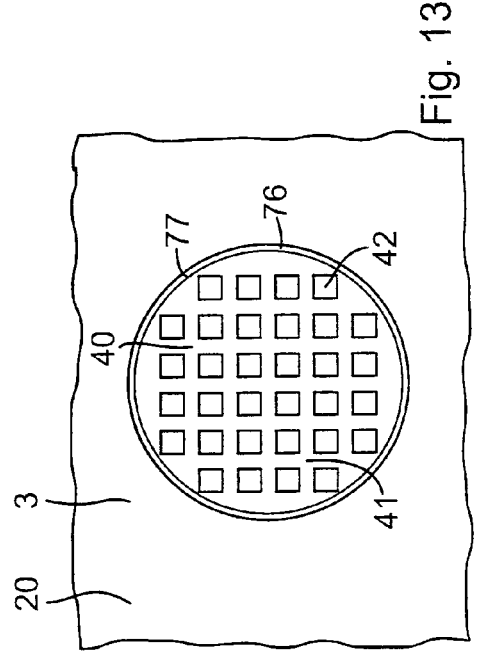
FIG. 13 is view similar to FIG. 5 and also not to scale of the micro-needle device of FIG. 11.

Referring now to FIGS. 11 to 13, there is illustrated a portion of a micro-needle device according to a further embodiment of the invention indicated generally by the reference numeral 75. The micro-needle device 75 is substantially similar to the micro-needle device 1 and similar components are identified by the same reference numerals. The main difference between the micro-needle device 75 and the micro-needle device 1 is that a means for effecting a seal between the first membrane 15 and the active substance layer 3 and the needle support layer 5 is provided. Additionally, a means for effecting a seal between the second membrane 16 and the active substance layer 3 and the drive substance layer 9 is provided, as is a means for effecting a seal between the drive substance layer 9 and the third membrane 17.

Each means for effecting the seal comprises an annular ridge type projecting element 76 extending from the corresponding one of the first and second major surfaces 20 and 21 of the active substance layer 3, the first and second major surfaces 37 and 38 of the drive substance layer 9, and from the second major surface 24 of the needle support layer 5. The annular projecting elements 76 extend around the corresponding ones of the active substance chambers 4, the drive substance chambers 10 and the membrane accommodating recesses 25 for sealably engaging the corresponding one of the first, second and third membranes 15, 16 and 17. Each annular projecting element 76 is of substantially semi-circular transverse cross-section and terminates in a radiused membrane abutting convex surface 77 for sealably abutting and engaging the adjacent one of the first, second and third membranes 16, 16 and 17.

The annular projecting elements 76 extending from the first major surface 20 of the active substance layer 3 and from the second major surface 24 of the needle support layer 5 co-operate with each other for sealably engaging and entrapping the first membrane 15 therebetween in order to sealably close the corresponding active substance chamber 4 adjacent the first major surface 20 of the active substance layer 3, thereby preventing leakage of active substance from one active substance chamber 4 to adjacent active substance chambers 4. The co-operating action of the annular projecting elements 76 on the first and second major surfaces 20 and 24 of the active substance layer 3 and the needle support layer 5, respectively, also prevents leakage of the active substance from one membrane accommodating recess 25 to adjacent ones of the memory accommodating recesses 25 during delivery of the active substance from the corresponding active substance chamber 4 through the corresponding micro-needle 6.

The annular projecting elements 76 extending from the second major surface 21 of the active substance layer 3 and from the first major surface 37 of the drive substance layer 9 co-operate with each other and sealably engage and trap the second membrane 16 therebetween for sealably closing the corresponding active substance chamber 4 and the corresponding drive substance chamber 10. The annular projecting elements 76 which extend from the second major surface 38 of the drive substance layer 9 co-operate with the first major surface 45 of the activation layer 12 for sealably engaging the third membrane 17 for in turn sealably closing the corresponding drive substance chamber 10.

In this embodiment of the invention the micro-needle device 75 is assembled in a similar manner as that of the micro-needle device 1, with the first membrane 15 located between the active substance layer 3 and the needle support layer 5, the second membrane 16 located between the active substance layer 3 and the drive substance layer 9, and the third membrane 17 located between the drive substance layer 9 and the activation layer 12. However, in this embodiment of the invention the assembly of the needle support layer 5, the active substance layer 3, the drive substance layer 9 and the activation layer 12 and the first, second and third membranes 15, 16 and 17 are held together by a suitable clamping arrangement which clamps the layers 3, 5, 9 and 12 tightly with the membranes 15 to 17 therebetween and with the annular projecting elements 76 tightly engaging the first, second and third membranes 15, 16 and 17 therebetween. The clamped assembly is then located in a frame or in a housing. Alternatively, the layers 3, 5, 9 and 12 with the membranes 15, 16 and 17 therebetween are ultrasonically welded together adjacent peripheral edges thereof.

The advantage of providing the annular projecting elements 76 on the second major surface 24 of the needle support layer 5, on the first and second major surfaces 20 and 21 of the active substance layer 3 and on the first and second major surfaces 37 and 38 of the drive substance layer 9 is that a good annular seal is effected between the corresponding layer 3, 5, 9 and 12 and the adjacent ones of the first, second and third membranes 15, 16 and 17 around the active substance chambers 4 and the drive substance chambers 10. The seal extends completely around the corresponding adjacent one of the active substance chamber 4 and the drive substance chamber 10, as well as and around the adjacent corresponding membrane accommodating recess 25, thereby preventing leakage of the active substance or the driving substance from the corresponding active and drive substance chambers 4 and 10 to adjacent active and drive substance chambers 4 and 10, and from the membrane accommodating recesses 25 to adjacent membrane accommodating recesses 25.

It is envisaged that in some embodiments of the invention the seal between the first membrane 15 and the active substance layer 3 and the needle support layer 5 may be achieved by annular projecting elements 76 extending from one of the first major surface 20 of the active substance layer 3 and the second major surface 24 of the needle support layer 5, and in which case, the annular projecting elements 76 would engage the first membrane 15 and co-operate with the other of the first major surface 20 and the second major surface 24 of the active substance layer 3 and the drive substance layer 9, respectively, for effecting the seal between the first membrane 15 and the respective active substance layer 3 and the needle support layer 5. In cases where annular projecting elements 76 are provided extending from only one of the first major surface 20 of the active substance layer 3 and the second major surface 24 of the needle support layer 5, it is envisaged that the annular projecting elements 76 will extend from the second major surface 24 of the needle support layer 5.

Similarly, it is envisaged that in certain cases, annular projecting elements 76 may be provided extending from only one of the second major surface 21 of the active substance layer 3 and the first major surface 37 of the drive substance layer 9 for engaging the second membrane 16, and in which case, it is envisaged that the annular projecting elements 76 will extend from the first major surface 37 of the drive substance layer 9.

Referring now to FIG. 14, there is illustrated a portion of a micro-needle device according to another embodiment of the invention, indicated generally by the reference numeral 80. The micro-needle device 80 is substantially similar to the micro-needle device 1 and similar components are identified by the same reference numerals. The main difference between the micro-needle device 80 and the micro-needle device 1 is that a means for effecting a seal between the first membrane 15 and the active substance layer 3 and the needle support layer 5 is provided, and a means for effecting a seal between the second membrane 16 and the active substance layer 3 and the drive substance layer 9 is also provided. In this embodiment of the invention the seal effecting means comprise pairs of interengageable complementary formations on the respective layers 3, 5 and 9. The pairs of interengageable complementary formations also act as alignment means for aligning the active substance layer 3 with the needle support layer 5 and the drive substance layer 9, so that the corresponding ones of the active and drive substance chambers 4 and 10 and the corresponding membrane accommodating recesses 25 are appropriately aligned with each other.

One of each pair of interengageable complementary formations comprising an annular alignment projecting element 81 extending from the corresponding one of first major surfaces 20 and 37 of the active substance layer 3 and the drive substance layer 9, respectively, which engages a corresponding alignment recess 82 formed in the corresponding one of second major surface 24 of the needle support layer 5 and in the second major surface 21 of the second layer 3. The alignment elements 81 extend around corresponding ones of the active and drive substance chambers 4 and 10, while the alignment recesses 82 extend around and into the corresponding ones of the membrane accommodating recesses 25 and the active substance chambers 4. The outer diameter of the alignment elements 81 and the inner diameter of the alignment recesses 82 are such as to accommodate the first and second membranes 15 and 16 therebetween when the needle support layer 5, the active substance layer 3 and the drive substance layer 9 are assembled together with the first and second membranes 15 and 16 located therebetween. Additionally, the alignment elements 81 and the alignment recesses 82 co-operate with each other to form a seal between first and second membranes 15 and 16 and the active substance layer 3 and the needle support layer 5 and the drive substance layer 19.

An additional advantage of providing the alignment elements 81 and the alignment recesses 82 between the active substance layer 3 and the needle support layer 5 is that they stretch the first membrane 15 taut across the active substance chambers 4 and the corresponding membrane accommodating recesses 25 which further enhances the reliability with which the pressure of the active substance at which the first membrane engages the puncturing members 33 and bursts can be set.

Figure 16:
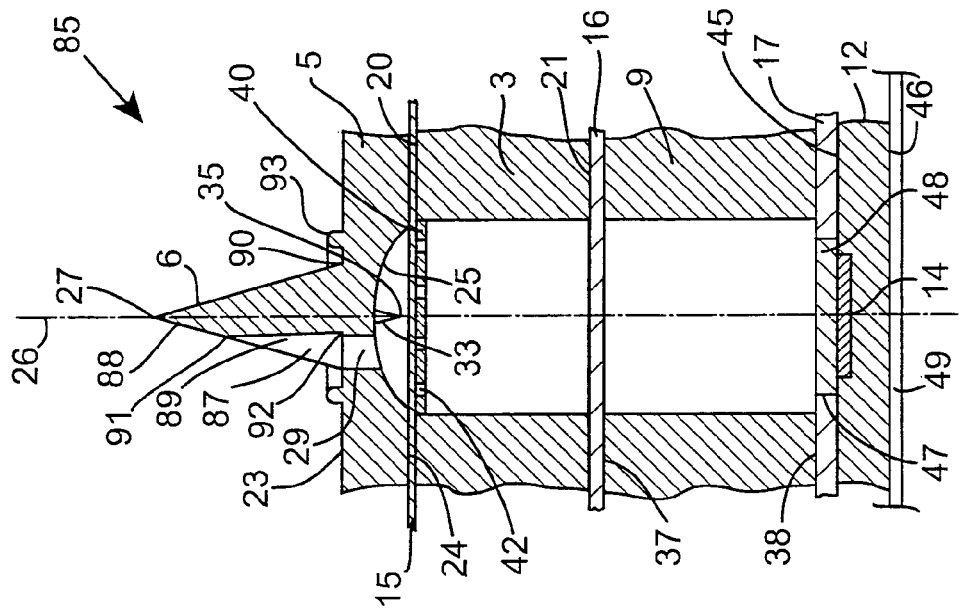
FIG. 16 is a view similar to FIG. 2, and also not to scale of a portion of the micro-needle device of FIG. 15.
Figure 15:
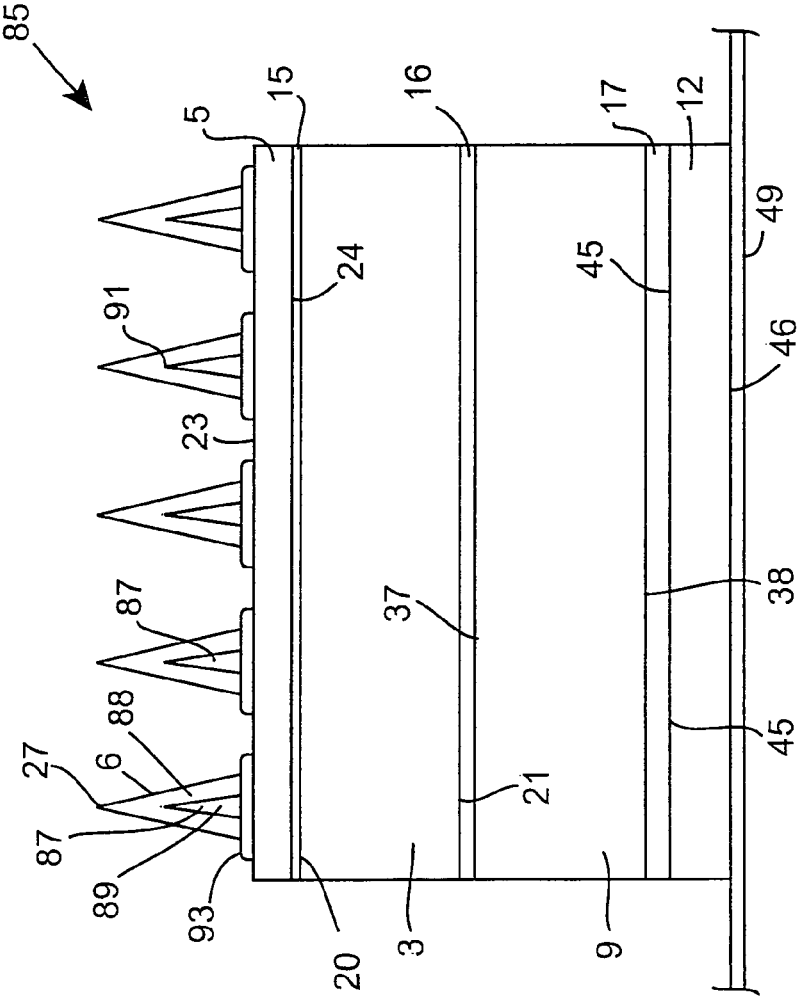
FIG. 15 is a side elevational view, not to scale, of a micro-needle device according to a still further embodiment of the invention.
Figure 17:
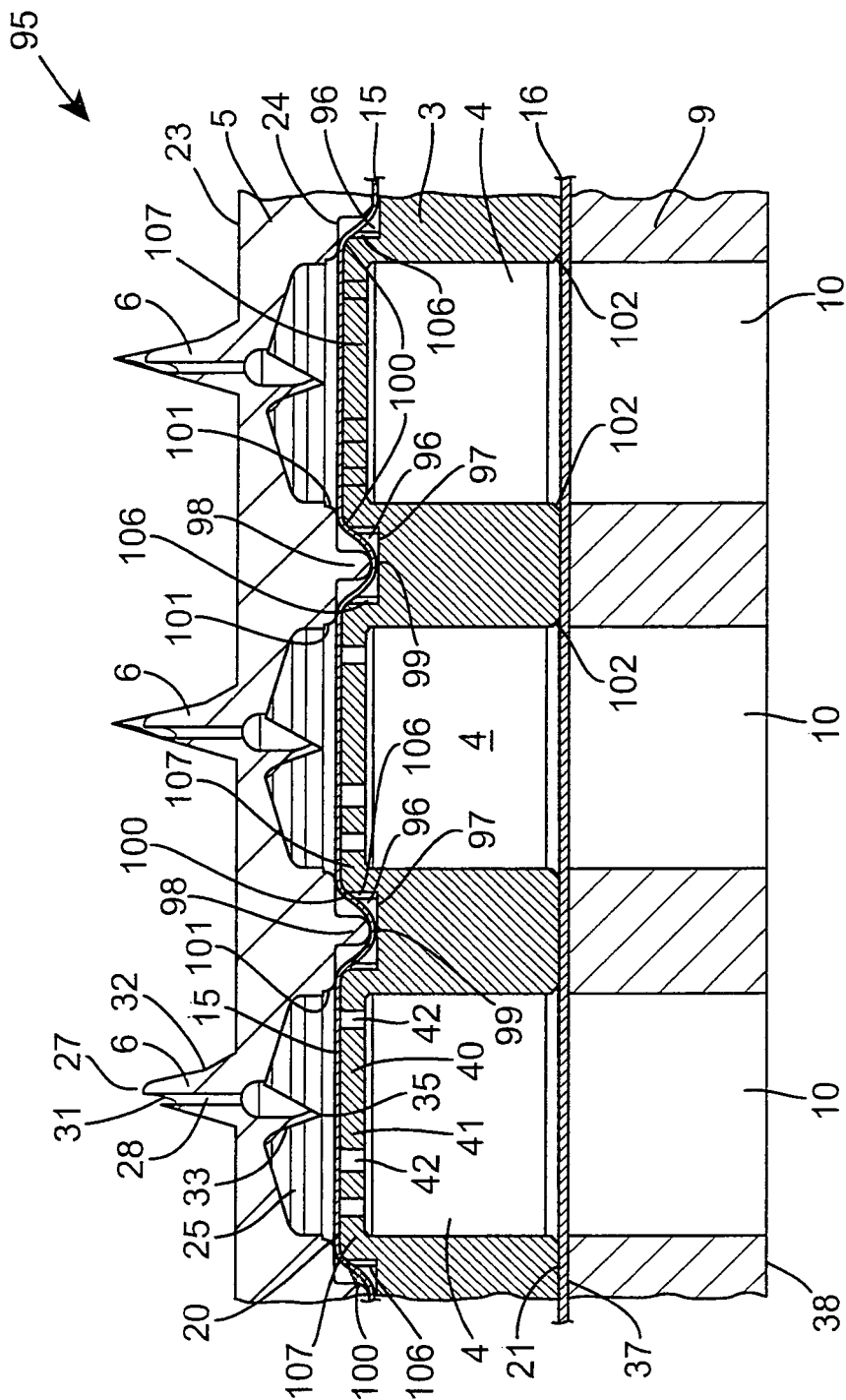
FIG. 17 is a cross-sectional side elevational view, also not to scale, of a portion of a micro-needle device according to another embodiment of the invention.
Figure 18:
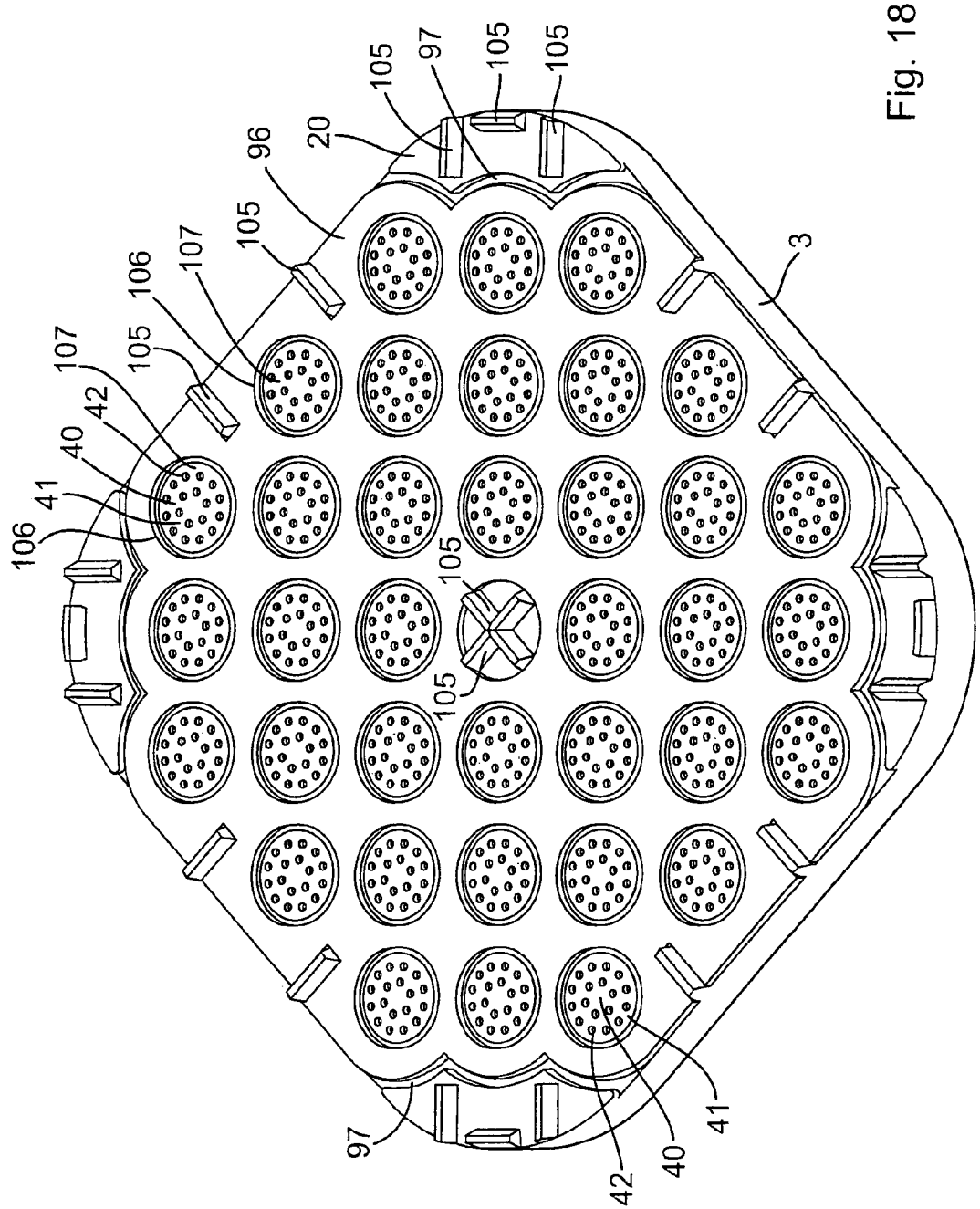
FIG. 18 is a top plan view of a detail of the micro-needle device of FIG. 17.
Figure 19:
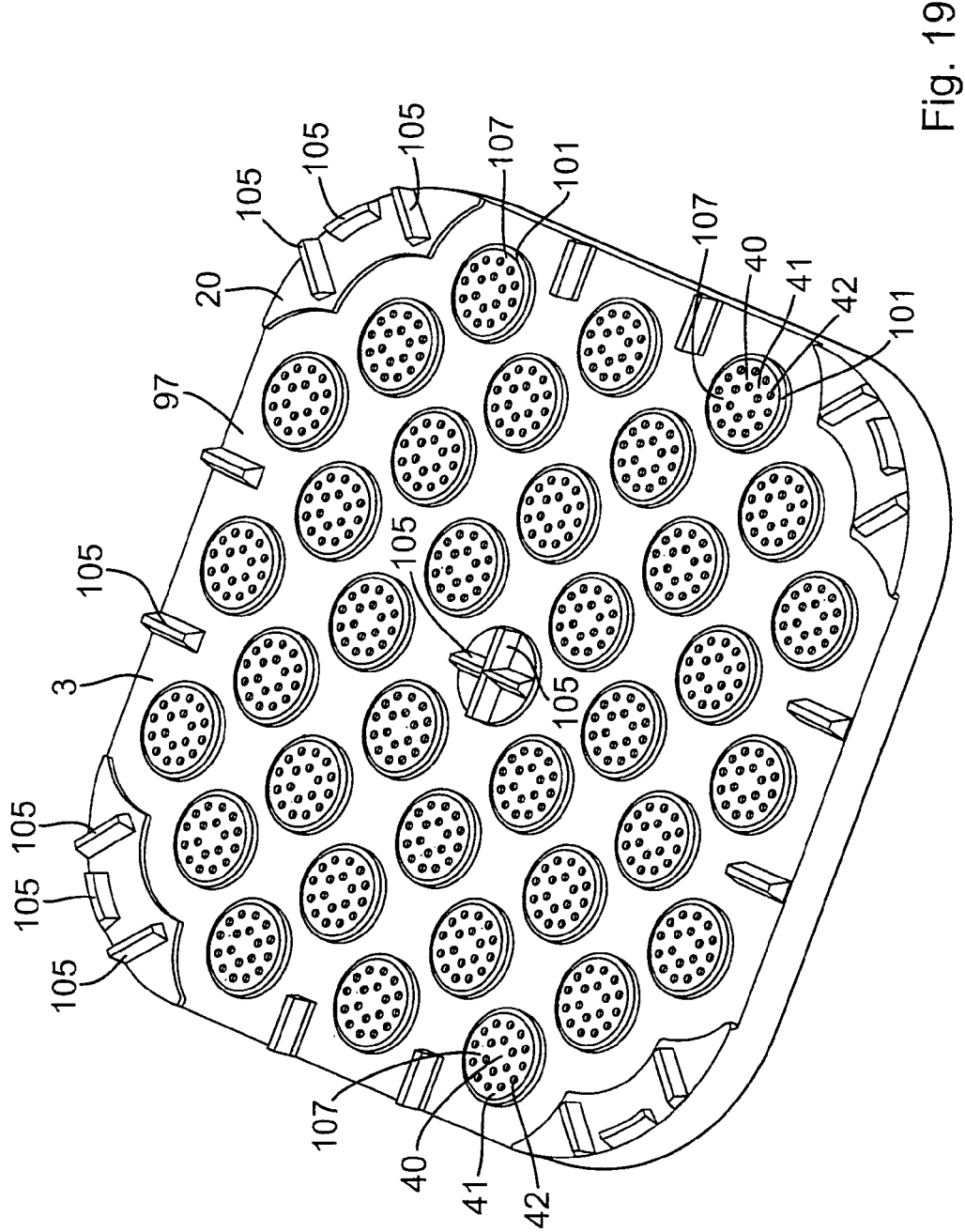
FIG. 19 is a top plan view of the detail of FIG. 18 of the micro-needle device of FIG. 17 with a portion of the detail removed.
Figure 20:
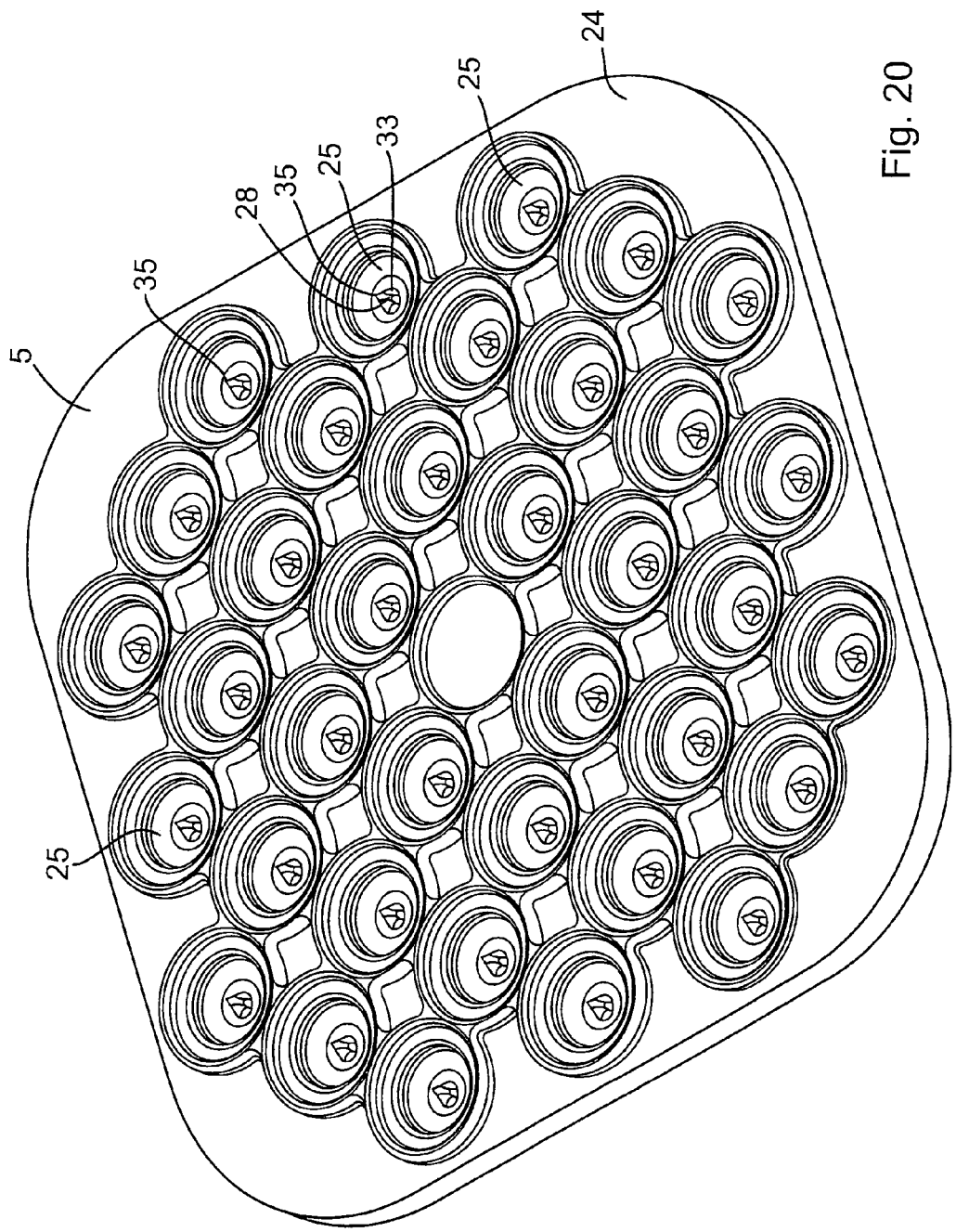
FIG. 20 is an underneath perspective view of another detail of the micro-needle device of FIG. 17.

Referring now to FIGS. 15 and 16, there is illustrated a micro-needle device according to another embodiment of the invention, indicated generally by the reference numeral 85. The micro-needle device 85 is substantially similar to the micro-needle device 1, and similar components are identified by the same reference numerals. The main difference between the micro-needle device 85 and the micro-needle device 1 is that instead of the communicating means for accommodating the active substance through the micro-needles 6 being provided by communicating bores extending through the respective micro-needles 6, in this embodiment of the invention each communicating means comprises the first portion 29 of the communicating bore 28 extending through the needle support layer 5, however the second portion of the communication bore 28 is replaced by a communicating channel 87 which communicates with the first portion 29 of the communicating bore 28 and extends along an outer surface 88 of the corresponding micro-needle 6. The communicating channel 87 of each micro-needle 6 is formed by a longitudinally extending recess 89 which extends in a generally axial direction along the corresponding micro-needle 6 from a proximal end 90 towards the distal tip 27 of the micro-needle 6, but terminates at a location 91 spaced apart from the distal tip 27 in order that the distal tip 27 is formed by a pointed tip. The first portion 29 of the communicating bore 28 extends through the needle support layer 5 from an area 92 in the first major surface 23 which is substantially defined by the communicating channel 87.

A sealing ring 93 extends from the first major surface 23 of the needle support layer 5 around each micro-needle 6, with the communicating channel 87 located within the sealing ring 93 for sealably abutting the skin of the subject in order to minimise leakage of the active substance as the active substance is passing from the first portion 29 of the communicating bore 28 into the communicating channel 87. Otherwise, the micro-needle device 85 is similar to the micro-needle device 1 and its use and operation is likewise similar.

Referring now to FIGS. 17 to 20, there is illustrated a micro-needle device according to another embodiment of the invention, indicated generally by the reference numeral 95. The micro-needle device 95 is substantially similar to the micro-needle device 1 and similar components are identified by the same reference numerals. The main difference between the micro-needle device 95 and the micro-needle device 1 is that a gasket 96 is located between the active substance layer 3 and the first membrane 15 to enhance sealing between the first membrane 15 and the active substance layer 3 and the needle support layer 5. A gasket accommodating recess 97 is formed into the first major surface 20 of the active substance layer 3, and the gasket 96 is recessed into the gasket accommodating recess 97. Openings 106 in the gasket 96 accommodate portions 107 of the active substance layer 3 therethrough and communicate the membrane accommodating recesses 25 with the active substance chambers 4. A plurality of annular projecting elements 98 extend from the second major surface 24 of the needle support layer 3 around the respective membrane accommodating recesses 25. The annular projecting elements 98 terminate in a radiused membrane abutting end 99 for sealably engaging the first membrane 15 and for urging the first membrane 15 into sealable engagement with the gasket 96, and for in turn urging the gasket 96 into sealable engagement with the active substance layer 3. The gasket 96 is of a deformable resilient material, in this embodiment of the invention silicone material of approximately 40 shore hardness. Thus, the gasket 96 accommodates any variations in the depth of the annular projecting elements 98 from the second major surface 24 of the needle support layer 5.

Accordingly, when the active substance layer 3 and the needle support layer 5 are assembled and tightly secured together with the gasket 96 in the gasket accommodating recess 97 and the first membrane 15 located between the needle support layer 5 and the gasket 96, the action of the annular projecting elements 98 urging the first membrane 15 into engagement with the gasket 96 and in turn urging the gasket 96 into engagement with the active substance layer 3 effects a good seal between the first membrane 15 and the gasket 96 and also between the gasket 96 and the active substance layer 3. Additionally, the action of the annular projecting elements 98 on the first membrane 15 also effects a good seal between the first membrane 15 and the needle support layer 5.

Additionally, when the active substance layer 3 and the needle support layer 5 are tightly secured together, the action of the annular projecting elements 98 on the first membrane 15 urging the first membrane 15 into the gasket 96 acts to stretch the first membrane 15 across the membrane accommodating recesses 25 so that the first membrane 15 is stretched taut across the membrane accommodating recesses 25. This, as described with reference to the micro-needle device 80 described with reference to FIG. 14, enhances the reliability and accuracy with which the pressure of the active substance at which the first membrane 15 engages the puncturing members 33 and bursts can be set.

Additionally, in this embodiment of the invention peripheral edges 100 of the gasket accommodating recess 97 in the active substance layer 3 are radiused adjacent the barrier panels 40 of the adjacent active substance chambers 4 to avoid any danger of rupturing of the first membrane 15 during assembly of the active substance layer 3 and the needle support layer 5. Peripheral edges 101 of the membrane accommodating recesses 25 in the needle support layer 5 are also radiused, to similarly avoid any danger of rupturing of the first membrane 15 during assembly of the active substance layer 3 and the needle support layer 5. Peripheral edges 102 of the active substance chambers 4 adjacent the second major surface 21 of the active substance layer 3 are radiused in order to avoid any danger of the second membrane 16 being ruptured as the second membrane 16 is being urged by the drive substance into the active substance chambers 3.

In this embodiment of the invention the piercing points 35 of the puncturing members 33 are centrally located in the corresponding membrane accommodating recesses 25. However, the micro-needles 6 are offset relative to the centre of the corresponding membrane accommodating recesses 25.

Additionally, in this embodiment of the invention securing lugs 105 extend from the first major surface 20 of the active layer 3 adjacent the periphery of the active substance layer 3 and also adjacent the centre of the active substance layer 3. The securing lugs 105 are of polymer material formed integrally with the active substance layer 3, and are fuseable with the second major surface 24 of the needle support layer 5 in response to ultrasonic welding. Thus, during ultrasonic welding of the active substance layer 3 to the needle support layer 5 when the active substance layer 3 and the needle support layer 5 are clamped together, the securing lugs partly melt and fuse to the active substance layer 3, in order to secure and retain the active substance layer 3 and the needle support layer 5 together, on removal of a clamp, with the first membrane 15 and the gasket 96 tightly clamped between the active substance layer 3 and the needle support layer 5. Although not shown, similar securing lugs may be provided extending from one or both of the second major surface 21 of the active substance layer 3 and the first major surface 37 of the drive substance layer 9 adjacent the peripheral edges and the centre thereof for similarly fusing and securing the active substance layer 3 and the drive substance layer 9 together with the second membrane 16 clamped therebetween in tight sealable engagement with the active substance and drive substance layers 3 and 9. Although not shown, similar securing lugs may be provided on the second major surface 38 of the drive substance layer 9 and/or on the first major surface 45 of the activation layer 12 for tightly and sealably securing the drive substance layer 9 and the activation layer 12 with the third membrane 17 tightly and sealably clamped therebetween.

Otherwise the micro-needle device 95 is similar to the micro-needle device 1 and its use and operation is likewise similar.

While the annular projecting elements of the micro-needle device 75 have been described as being in sealable engagement with the adjacent membrane whereby the sealing engagement is achieved by compression, it is envisaged in certain cases that the annular projecting elements may be bonded to the adjacent membrane. However, when bonding is provided between the annular projecting elements and the adjacent membrane, it is also envisaged that compression would also be relied on in order to maintain the respective needle support layer, the active substance layer, the drive substance layer and the activating layer assembled together with the respective first, second and third membranes secured together. Such a clamping arrangement may be provided by a clamping frame within which the assembled layer 3, 5, 9 and 12 together with the membranes 15, 16 and 17 would be located.

While the micro-needle devices according to the invention have been described as comprising active substance layers, drive substance layers and needle support layers of polymer materials, the active substance layer, the drive substance layer and the needle support layer may be of any other suitable material. Needless to say, the activation layer may be of a material other than ceramics or a material suitable for forming a printed circuit board. It is envisaged that the activation layer may be of a polymer material.

While the micro-needles of the micro-needle device 85 have been described as comprising communicating channels extending in a generally axial direction along the outer surface of the micro-needles, it is envisaged that the communicating channels may extend in the form of a spiral around the outer surface of the micro-needles.

While the micro-needle devices according to the invention have been described as comprising a particular type of puncturing means, any other suitable puncturing means may be provided. For example, it is envisaged that the puncturing means may terminate in a piercing tip, which instead of being pointed, may be of annular shape with a cutting edge, which would form an opening in the first membrane. It is also envisaged that the puncturing means may terminate in an elongated knife edge or a serrated saw-type edge for engaging and piercing the first membrane. Further, it is envisaged that where the puncturing means terminates in a knife edge or a serrated saw-type edge, the knife edge or serrated saw-type edge could be inclined relative to the plane defined by the second major surface of the needle support layer to facilitate progressive engagement of the first membrane with the knife edge or serrated saw-type edge to further enhance rupturing of the first membrane.

It is also envisaged that each puncturing member may terminate in a partly annular cutting edge, which would extend partly around and adjacent the periphery of the corresponding membrane accommodating recess, in order to partly sever a portion of the first membrane from the first membrane adjacent the corresponding membrane accommodating recess, for communicating the communicating bore or channel of the micro-needle with the corresponding active substance chamber.

It is also envisaged that the first membrane may be provided with small areas of weakness at respective locations corresponding to the locations which would be engaged by the puncturing means when the active substance in the corresponding active substance chamber is pressurised for urging the first membrane into engagement with the puncturing means.

From the above description of the micro-needle devices it will be readily apparent to those skilled in the art that by varying the length of the puncturing member, which in turn varies the distance of the piercing point of the puncturing member from the plane defined by the second major surface of the needle support layer, the pressure of the active substance at which the first membrane bursts can be varied, which in turn allows the pressure at which the active substance is delivered through the communicating bore or the communicating channel of the corresponding micro-needle to be controlled. As discussed above, by varying the pressure at which the active substance is delivered through the micro-needles, the injection velocity of the active substance into the subject can also be varied, thereby allowing the depth to which the active substance is delivered beneath the skin of the subject to be set.

It is also envisaged that the puncturing means may be provided to be adjustable for selectively varying the distance d of the piercing point or tip of the puncturing member from the plane defined by the second major surface of the needle support layer. Such adjustability could be achieved by providing each puncturing member as an elongated spindle which would be axially moveable in a corresponding bore through the needle support layer into the corresponding membrane accommodating recess. The spindle of the puncturing member may be threaded and would engage corresponding threads in the corresponding bore of the needle support layer for facilitating selective adjustment of the distance d of the piercing point or tip of the puncturing member from the plane defined by the second major surface of the needle support layer.

While the puncturing means has been described as being located in the needle support layer, it is envisaged that the puncturing means may be provided in the active substance layer, and this would be a particular requirement where the micro-needle device is to be used, or where some of the active substance chambers of the micro-needle device are to be used for withdrawing a substance, for example, blood or other bodily fluid from a subject. In which case, it is envisaged that the micro-needle device would be provided with the second membrane stretched into the active substance chambers and defining the active substance chambers, which could be under vacuum, or alternatively, the second membrane could be pressurised by the driving substance in the corresponding drive substance chambers. In this configuration of the micro-needle device, the barrier panel would be omitted from the active substance chambers, and the puncturing member would be located within the active substance chamber with a puncturing point adjacent but spaced apart from the first membrane. The drive substance would be of a material which on being activated would contract. Thereby on being activated by a suitable activating means, contraction of the drive substance would urge the second membrane out of the active substance chamber, thereby reducing the pressure in the active substance chamber. The reduction in pressure in the active substance chamber would urge the first membrane to balloon into the active substance chamber, which in turn would be engaged by the piercing point of the puncturing member, which would then communicate the low pressure or evacuated active substance chamber through the communicating bore or channel of the corresponding micro-needle with a location beneath the skin of the subject for withdrawing the bodily fluid from the subject.

It is also envisaged that the micro-needle device may be provided with a means for analysing the bodily fluid so withdrawn from the subject. The microprocessor of the micro-needle device may be programmed that in response to the analysis of the bodily fluid so withdrawn, one or more of the activating means which correspond to active substance chambers which contain a suitable active substance would be activated to deliver the active substance from the corresponding active substance chamber to the subject.

While the activating means have been described as comprising heating elements, any other suitable activating means besides heating elements may be provided. In certain cases, it is envisaged that the activating means may be an element for cooling or chilling the drive substance. In which case, the drive substance could, for example, be provided by a fluid which rapidly contracted on being activated, for example, on being subjected to a reduction in temperature. In which case, the activating means would be provided to reduce the temperature of the drive substance, instead of raising the temperature of the drive substance.

It will also be appreciated that while the drive substance has been described as comprising gas filled microspheres sold under the Trade Mark EXPANCEL, gas filled polymer microspheres sold under other Trade Marks may be used, and needless to say, other suitable drive substances may be used, for example, the drive substance may be a gas, or may be provided by a liquid which rapidly transitions from the liquid phase to the gaseous phase on being heated, alternatively, the drive substance may be provided by a porous polymer impregnated with a gas, which on being heated either causes the polymer material to rapidly expand, or causes the gas to migrate from the porous polymer material as it expanded for in turn urging the second membrane into the corresponding active substance chambers. It is also envisaged that the drive substance may be provided in the form of a solid propellant, such as, for example, AIBN.

It will be appreciated that while the micro-needle devices have been described for delivering a liquid medicament into a subject, the micro-needle devices may be used for delivering any suitable medicament or substance, whether in liquid or gaseous form into a subject.

It will also be appreciated that while the micro-needle device has been described for transferring fluid between the active substance chambers and a subject, which may be a human or animal subject, it is envisaged that the micro-needle device may be used for transferring a fluid between the first chamber and any other non-human or non-animal object or device.

While the fluid transfer devices according to the invention have been described as being micro-needle devices, the fluid transfer devices may be of any other suitable configuration. For example, any other suitable penetrating means for penetrating the skin of a subject besides micro-needles extending from the skin abutting layer may be provided, and such penetrating means may, for example, be provided by roughening the first major surface of the skin abutting layer. In which case, it is envisaged that the communicating means would be provided by communicating bores extending through the skin abutting layer from the corresponding membrane accommodating recesses to the first major surface of the skin abutting layer.

It will also be appreciated that while the micro-needles have been described as being of conical shape, the micro-needles may be of any other suitable or desired shape, and in certain cases, may be of transverse cross-section other than circular, for example, square, rectangular, hexagonal, octagonal, polygonal or any other suitable or desired shape, cross-section or configuration, and where the micro-needles are of square cross-section, the micro-needles would be of pyramid form. It is also envisaged that the micro-needles may be of partly conical and partly pyramid shape.

It is also envisaged that the first membrane may be provided with a plurality of areas of weakness, the locations of which would typically correspond with the locations of the distal end of the corresponding puncturing member, so that on engagement of the area of weakness of the first membrane with the distal piercing end of the corresponding puncturing member, the weakened area would be punctured, or alternatively, the distal piercing end of the puncturing member would cause rupturing of the first membrane adjacent the corresponding first chamber. Indeed, in certain cases, it is envisaged that arcuate lines of weakness, for example, partly annular lines of weakness could be provided in the first membrane which would extend in a partly annular shape around and typically adjacent the periphery of the corresponding first membrane accommodating recesses. In which case, the cutting edge of the puncturing member may be correspondingly shaped of partially annular shape and would be configured to engage the corresponding line of weakness for rupturing the first membrane along the line of weakness. Indeed, where the first membrane is provided with such areas or lines of weakness, while it would most likely be preferable, it would not be essential that the cutting edge should correspond exactly with the line of weakness. In certain cases, a pointed distal tip may be sufficient to cause rupturing of the first membrane along the entire line of weakness. Such an arrangement of lines of weakness in the first membrane and correspondingly shaped cutting edges of the puncturing members would be particularly advantageous in cases where the first membrane is provided as a foil material, such as a metal foil.

While the first and second layers have been described and illustrated as being of similar thickness, the thickness of the active and drive substance layers may be the same or different. Indeed, in certain cases, it is envisaged that the drive substance layer may be thinner than the active substance layer or vice versa, and this would largely depend on the type of drive substance being used. Where gas filled spheres of the type sold under EXPANCEL is provided as the drive substance, and since such gas filled spheres can expand up to four times and more their normal size, it is envisaged that the thickness of the drive substance layer may be less than the thickness of the active substance layer.

Additionally, while the active and drive substance chambers have been described as being of circular transverse cross-section, the first and second chambers may be of any desired cross-section.

It is also envisaged that a spacer layer, which typically would be of a polymer material, may be provided located between the needle support layer 5 and the first membrane 15. The spacer layer would be provided with openings corresponding to and aligned with the membrane accommodating recesses 25, and the openings in the spacer layer would typically be of diameter similar to the diameter of the membrane accommodating recesses 25 for accommodating the first membrane into the membrane accommodating recesses 25 in the needle support layer 5. The advantage of providing such a spacer layer between the needle support layer 5 and the first membrane 15 is that it would facilitate increasing the distance d between the piercing points 35 of the puncturing members 53 and the first membrane 15. This would result in an increase in the pressure of the active substance within the active substance chambers 4 at which the first membrane 15 engaged the piercing points 35 of the puncturing members 33, and thus, would allow the predefined pressure of the active substance in the active substance chambers 4 at which the first membrane 15 bursts to be set at a higher pressure, for in turn increasing the injection velocity at which the active substance is injected into the subject. It is also envisaged that spacer layers of different thicknesses may be provided, so that the injection velocity of the active substance could be set by selecting a spacer element of the appropriate thickness for locating between the needle support layer 5 and the first membrane 15.

While the micro-needle devices have been described as comprising an activation layer which is separate from the drive substance layer, in certain cases, it is envisaged that the activation layer may be formed integrally with the drive substance layer. In which case the heating elements or other activating means together with the corresponding circuitry would be appropriately located in or on the portion of the drive substance layer which forms the activation layer. By integrally forming the drive substance and activation layers, the need for the third membrane would be avoided.

While in general the micro-needle devices according to the invention have been described with the active substance layer, the drive substance layer, the needle support layer and the activation layer secured together by clamping or by ultrasonic welding, in certain cases, it is envisaged that the respective layers may be bonded to the corresponding membrane by a suitable bonding agent, for example, a suitable adhesive. However, the advantage of securing the layers together with the membranes located therebetween by clamping or by ultrasonic welding is that the need for adhesive or other such bonding agents is avoided, and this could be advantageous in certain cases where the active substance would react with certain adhesives or bonding agents.

While the micro-needle devices have been described as comprising a plurality of micro-needles, active substance chambers, drive substance chambers and activating means, it is envisaged that a micro-needle device may be provided with one single micro-needle, one single active substance chamber, one single drive substance chamber and one single activating means. It is also envisaged that in certain cases the numbers of micro-needles, active substance chambers, drive substance chambers and activating means may be different in the one micro-needle device. For example, in certain cases, it is envisaged that more micro-needles may be provided than active substance chambers. Alternatively, less micro-needles than active substance chambers may be provided. Similarly, more or less drive substance chambers than active substance chambers may be provided, and additionally, more or less activating means than drive substance chambers may be provided.

The invention claimed is:
1. A fluid transfer device comprising:
 a first layer having a first face and a second face and a first chamber located in the first layer, the first chamber extending into the first layer from the second face thereof, a skin abutting layer having a first face for abutting skin of a subject and a second face located adjacent the first face of the first layer, a communicating means in the skin abutting layer for accommodating a fluid from the first chamber to the subject, a first membrane located between the first face of the first layer and the second face of the skin abutting layer for isolating the communicating means from the first chamber, a second membrane located adjacent the second face of the first layer for closing the first chamber adjacent the second face of the first layer, a pressure altering means co-operable with the second membrane for urging the second membrane into the first chamber to increase the pressure in the first chamber for urging the fluid from the first chamber to the subject through the communicating means, a puncturing means located in the skin abutting layer to be engageable with the first membrane for bursting thereof in response to the second membrane being urged into the first chamber for increasing the pressure in the first chamber, and a barrier means which is permeable to the fluid in the first chamber located in the first chamber for preventing engagement of the second membrane with the puncturing means.

2. A fluid transfer device as claimed in claim 1 in which the puncturing means extends from the skin abutting layer and terminates in a piercing means for piercing the first membrane.

3. A fluid transfer device as claimed in claim 2 in which a membrane accommodating recess extends into the skin abutting layer from the second face thereof, and the puncturing means extends from the skin abutting layer into the membrane accommodating recess towards the first membrane.

4. A fluid transfer device as claimed in claim 2 in which the spacing between the piercing means and the first membrane is set to determine the pressure in the first chamber at which the first membrane bursts.

5. A fluid transfer device as claimed in claim 1 in which the first membrane comprises a burstable material.

6. A fluid transfer device as claimed in claim 1 in which the second membrane comprises a stretchable material.

7. A fluid transfer device as claimed in claim 1 in which the barrier means is located adjacent the first face of the first layer.

8. A fluid transfer device as claimed in claim 1 in which a micro-needle extends from the first face of the skin abutting layer and communicates with the communicating means.

9. A fluid transfer device as claimed in claim 1 in which the barrier means comprises a perforated barrier panel defining a plurality of openings extending therethrough, the openings being of size to accommodate the fluid to be transferred from the first chamber to the subject, but to prevent the second membrane passing therethrough.

10. A fluid transfer device comprising:
a first layer having a first face and a second face and a first chamber extending into the first layer from the second face thereof, a skin abutting layer having a first face for abutting skin of a subject and a second face located adjacent the first face of the first layer, a communicating means in the skin abutting layer for accommodating a fluid between the first chamber and the subject, a second layer having a first face and a second face and a second chamber extending into the second layer from the first face thereof to the second face thereof, the second layer being located adjacent the first layer with the first face of the second layer adjacent the second face of the first layer, an activation layer defining a first face and located adjacent the second layer with the first face of the activation layer adjacent the second face of the second layer, a first membrane located between the first face of the first layer and the second face of the skin abutting layer for isolating the communicating means in the skin abutting layer from the first chamber in the first layer, a second membrane located between the second face of the first layer and the first face of the second layer for closing the first chamber adjacent the first face of the first layer and for closing the second chamber adjacent the first face of the second layer, a third membrane located between the second face of the second layer and the first face of the activation layer for sealably closing the second chamber of the second layer adjacent the second face thereof, a pressure altering means located in the second chamber of the second layer, the pressure altering means being co-operable with the second membrane for urging the second membrane relative to the first chamber for altering the pressure in the first chamber for urging the fluid between the first chamber and the subject through the communicating means, a puncturing means located in one of the skin abutting layer and the first layer to be engageable with the first membrane for bursting thereof in response to the pressure altering means altering the pressure in the first chamber, and an activating means located in the activation layer adjacent the first face thereof for activating the pressure altering means in the second chamber of the second layer for altering the pressure in the second chamber.

11. A fluid transfer device as claimed in claim 10 in which the activating means comprises an electrically powered heating element.

12. A fluid transfer device as claimed in claim 10 in which the activating means comprises a heating means.

13. A fluid transfer device as claimed in claim 12 in which the third membrane is of a heat insulating material, and a heat conducting means extends through the third membrane for conducting heat from the heating means to the second chamber.

14. A fluid transfer device as claimed in claim 10 in which the device is adapted for transferring a fluid from the first chamber to the subject, and the fluid comprises a liquid active substance.

15. A fluid transfer device comprising:
a first layer having a first face and a second face and a plurality of first chambers configured in a matrix extending into the first layer from the second face thereof, a skin abutting layer having a first face for abutting the skin of a subject and a second face located adjacent the first face of the first layer, a plurality of communicating means in the skin abutting layer corresponding to the respective first chambers in the first layer, each communicating means communicating with the corresponding one of the first chambers for accommodating a fluid between the corresponding first chamber and the subject, a second layer having a first face and a plurality of second chambers corresponding to the respective first chambers in the first layer, each second chamber extending into the second layer from the first face thereof, a first membrane located between the first face of the first layer and the second face of the skin abutting layer for isolating the communicating means from the corresponding first chambers, a second membrane located between the second face of the first layer and the first face of the second layer for closing the first chambers adjacent the second face of the first layer and for closing the second chambers adjacent the first face of the second layer, a plurality of pressure altering means located in the respective second chambers, each pressure altering means being co-operable with the second membrane for urging the second membrane relative to the corresponding one of the first chambers in the first layer for altering the pressure in the corresponding first chamber for urging the fluid between the corresponding first chamber and the subject through the corresponding communicating means, a plurality of puncturing means corresponding to the respective first chambers, the puncturing means being located in one of the skin abutting layer and the first layer to be engageable with the first membrane in response to one of the pressure altering means altering the pressure in the corresponding second chamber for bursting a portion of the first membrane to communicate the first chamber corresponding to the second chamber within which the pressure is altered with the corresponding communicating means, and a plurality of micro-needles corresponding to the respective communicating means extending from the first face of the skin abutting layer, each micro-needle communicating with a corresponding one of the communicating means in the skin abutting layer.

16. A fluid transfer device as claimed in claim 15 in which each pressure altering means comprises a drive substance in the corresponding second chamber adapted to expand for urging the second membrane to increase the pressure in the first chamber.

17. A fluid transfer device as claimed in claim 15 in which the second chambers are aligned with the respective first chambers.

18. A fluid transfer device as claimed in claim 15 in which each puncturing means extends from the one of the skin abutting layer and the first layer and terminates in a corresponding piercing means for piercing the first membrane.

19. A fluid transfer device as claimed in claim 18 in which a plurality of membrane accommodating recesses corresponding to the respective first chambers extends into the skin abutting layer from the second face thereof, and the puncturing means extends from the skin abutting layer into the respective membrane accommodating recesses towards the first membrane, and the piercing means of the respective puncturing means are located within the membrane accommodating recess adjacent a plane defined by the second face of the skin abutting layer, and slightly spaced apart therefrom.

20. A fluid transfer device as claimed in claim 19 in which each membrane accommodating recess is aligned with the corresponding one of the first chambers.

21. A fluid transfer device as claimed in claim 18 in which the spacing between each piercing means and the first membrane is set to determine the pressure in the corresponding first chamber at which the first membrane bursts.

22. A fluid transfer device as claimed in claim 15 in which each micro-needle is aligned with the corresponding one of the first chambers.

* * * * *